US010881081B2

(12) United States Patent
Hall et al.

(10) Patent No.: US 10,881,081 B2
(45) Date of Patent: Jan. 5, 2021

(54) AUTONOMOUS FEED DELIVERY PLATFORM FOR INSECTS

(71) Applicant: ASPIRE FOOD GROUP LTD, Toronto (CA)

(72) Inventors: Michael Todd Hall, Austin, TX (US); Gabriel Mott, Austin, TX (US); Mohammed Ashour, Austin, TX (US)

(73) Assignee: ASPIRE FOOD GROUP LTD, Toronto (CA)

( * ) Notice: Subject to any disclaimer, the term of this patent is extended or adjusted under 35 U.S.C. 154(b) by 0 days.

(21) Appl. No.: 15/187,132

(22) Filed: Jun. 20, 2016

(65) Prior Publication Data

US 2017/0360014 A1 Dec. 21, 2017

(51) Int. Cl.
| | | |
|---|---|---|
| *A01K 5/02* | (2006.01) | |
| *B65G 1/04* | (2006.01) | |
| *G05D 1/00* | (2006.01) | |
| *G05D 1/02* | (2020.01) | |
| *A01K 67/033* | (2006.01) | |

(52) U.S. Cl.
CPC ............. *A01K 5/02* (2013.01); *A01K 5/0266* (2013.01); *B65G 1/0492* (2013.01); *G05D 1/0022* (2013.01); *G05D 1/0219* (2013.01); *A01K 67/033* (2013.01)

(58) Field of Classification Search
CPC .......... A01K 5/00; A01K 5/02; A01K 5/0208; A01K 5/0216; A01K 5/0225; A01K 5/0266; A01K 5/0275; A01K 5/0283; A01K 5/0291

See application file for complete search history.

(56) References Cited

U.S. PATENT DOCUMENTS

| | | | |
|---|---|---|---|
| 3,087,461 A | | 4/1963 | Strand et al. |
| 3,273,539 A | | 9/1966 | Cooper et al. |
| 4,002,252 A | * | 1/1977 | Beckman, Jr. ....... A01K 5/0266 414/501 |
| 4,141,321 A | * | 2/1979 | Wolf .................... A01K 5/0283 119/56.1 |
| 4,337,729 A | | 7/1982 | Peppler et al. |
| 4,523,547 A | | 6/1985 | Ogasawara et al. |
| 5,879,029 A | * | 3/1999 | Wilks .................... F16L 11/121 285/131.1 |
| 6,200,017 B1 | * | 3/2001 | van den Berg .......... A01K 5/00 119/521 |
| 6,997,666 B1 | * | 2/2006 | Rodgers ................. B65G 67/24 414/331.06 |

(Continued)

FOREIGN PATENT DOCUMENTS

| | | | |
|---|---|---|---|
| GB | 1564197 | * | 4/1980 |
| WO | 2016/015639 A1 | | 4/2016 |

OTHER PUBLICATIONS

PCT International Search Report and the Written Opinion for Application No. PCT/17/38351, dated Nov. 2, 2017, 10 pages.

(Continued)

*Primary Examiner* — Thanh Pham
(74) *Attorney, Agent, or Firm* — Lee & Hayes, P.C.

(57) ABSTRACT

An autonomous feed delivery platform configured to navigate through a facility and deliver insect feed to multiple insect habitats located within the facility. In some cases, the feed delivery platform may be configured to deliver the feed to multiple insect habitats at substantially the same time.

20 Claims, 20 Drawing Sheets

(56) References Cited

U.S. PATENT DOCUMENTS

| | | | | |
|---|---|---|---|---|
| 2003/0070622 A1* | 4/2003 | Vaags | ............... | A01K 5/0266 |
| | | | | 119/51.11 |
| 2005/0193954 A1* | 9/2005 | Cureton | ............... | A01K 5/02 |
| | | | | 119/53 |
| 2007/0266959 A1* | 11/2007 | Brooks | ............... | A01K 11/008 |
| | | | | 119/720 |
| 2009/0050063 A1* | 2/2009 | Chang | ............... | A01K 5/00 |
| | | | | 119/51.01 |
| 2009/0050067 A1* | 2/2009 | Parsons | ............... | G06Q 99/00 |
| | | | | 119/200 |
| 2010/0307421 A1* | 12/2010 | Gates | ............... | A01K 5/0225 |
| | | | | 119/56.1 |
| 2012/0104032 A1* | 5/2012 | Bahn | ............... | B65B 1/12 |
| | | | | 222/1 |
| 2013/0319334 A1* | 12/2013 | Newton | ............... | A01K 67/033 |
| | | | | 119/6.5 |
| 2014/0116343 A1* | 5/2014 | Collins | ............... | A01K 5/0225 |
| | | | | 119/51.11 |
| 2014/0261199 A1* | 9/2014 | Rose | ............... | A01K 5/02 |
| | | | | 119/53 |
| 2015/0149050 A1* | 5/2015 | Palsgaard | ............... | A01K 5/00 |
| | | | | 701/50 |
| 2018/0352793 A1 | 12/2018 | Hall et al. | | |

OTHER PUBLICATIONS

The Extended European Search Report dated Apr. 22, 2020 for European Patent Application No. 17816068.5, 8 pages.

* cited by examiner

AUTONOMOUS FEED DELIVERY PLATFORM FOR INSECTS

BACKGROUND

Today most insects that are cultivated for human consumption are housed in single use cardboard boxes or immobile large troughs made of wood or concrete. The insects housed within the boxes are typically fed by replacing food trays by hand. Unfortunately, when food trays are removed, the insects: particularly with larva or baby insects that are hard to see, are removed with the tray decreasing the overall populations. Additionally, human interaction with the insects may lead to damage, such as crushing or smashing of the insects. Interaction can also cause passing of pathogens between populations.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
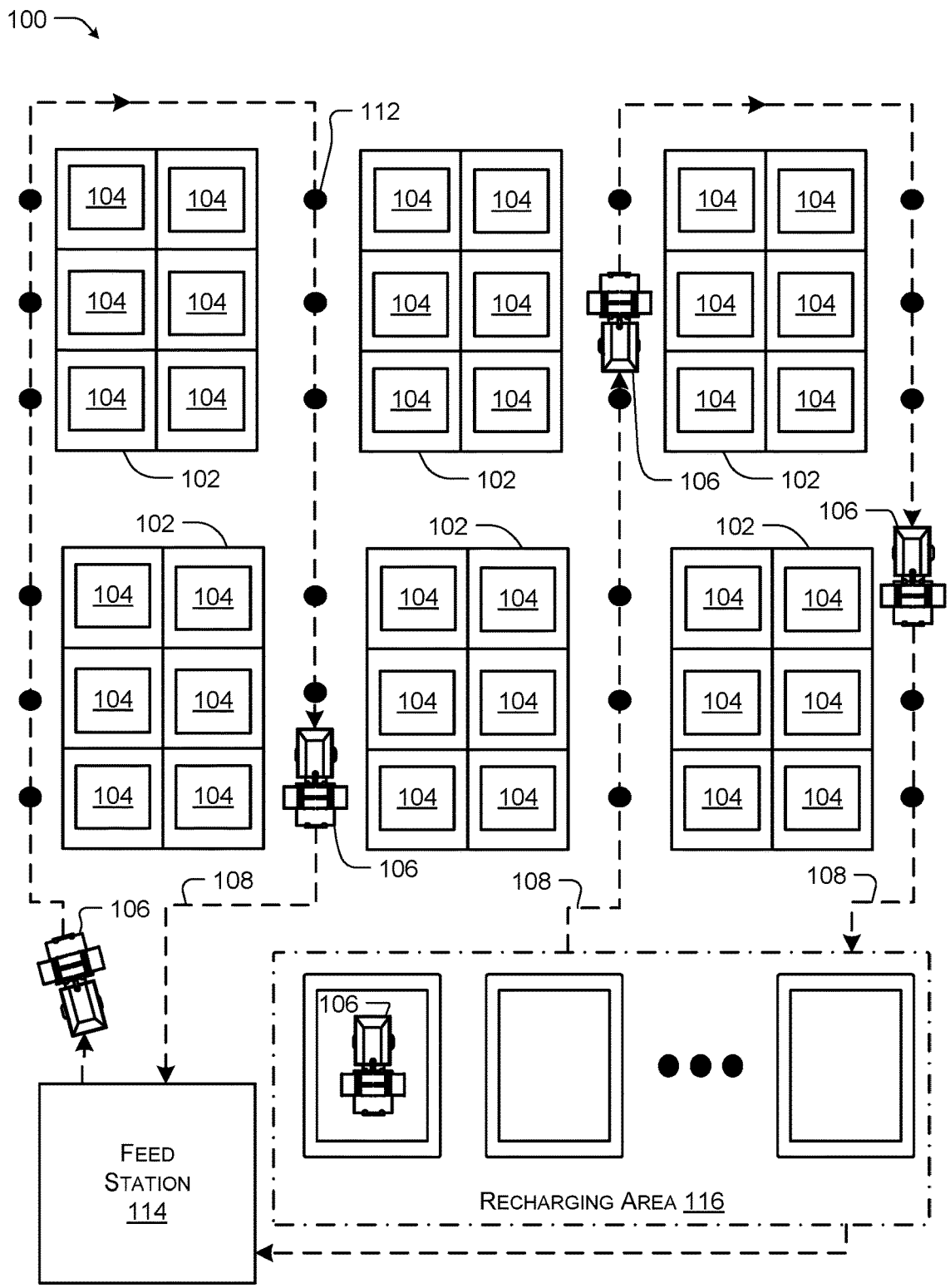
FIG. 1 illustrates an example facility having multiple racks of insect habitats and feed delivery platforms for cultivating insects according to some implementations.

Described herein are implementations and techniques for providing automated platforms or vehicles for feeding insects. For example, live insects may be cultivated in habitats containing individual populations. Each habitat may include a feed plate or apparatus that the insects within the habitat may access from time to time. Periodically, the feed plate or apparatus should be replaced or filled. Traditionally, the feed plates may include a paper plate filled with feed and set inside the habitat. When the feed is consumed, a human may remove the paper plate and any remaining feed from the habitat and replace the empty plate with a new paper plate filled with feed. Unfortunately, live insects may cling to the empty plate as the plate is removed, thereby reducing the population. Additionally, the human interaction with the insects may pass pathogens from habitat to habitat or crush or smash the insects within the habitats, particularly, during the insects' early developmental stages.

In some implementations described herein, a feed delivery platform or vehicle may be configured to navigate or traverse through a facility to deliver feed to the various habitats contained within the facility. For example, the facility may be outfitted with a rack system configured to hold or house multiple insect habitats in vertical rows to increase the overall output of the facility. In general, the rack system is designed to improve the efficiency of cultivating live insects, such as crickets, grasshoppers, mealworms, and other insets that have a flightless stage, and to minimize the insects' exposure to human interaction or contact in addition to the autonomous feed deliver platform. In some instances, the vertical racks may be placed adjacent to or side-by-side. The racks may also be grouped such that various groups of racks may support habitats that each contain insects in the same stage of development (e.g., each habitat in the group contains eggs, larvae, infants or pin heads, adolescents, or adult insects). In these instances, each feed delivery platform may be configured to provide feed in a manner that supports the particular life stage of the insects within the assigned group of habitats or racks.

In some cases, each habitat may also be designed with a dividing insert or unit. The insert may be included to increase the overall total surface area within the same volume previously contained within the habitat, thereby improving overall yields per-volume. The habitat inserts generally form a grid, helix or cross-section within the interior space of the habitat. In some cases the inserts are designed to be removable from the habitat. Thus the vertical wall design of the inserts may assist with harvesting of the insects when the insert is removed from the habitat. For example, the inserts may be moved over a bin and vibrated to cause the insects to fall off of or detach from the vertical surfaces of the insert.

Additionally, the inserts may be configured to receive a feed dais into a depressed region on the top surface of the insert at predetermined locations. The dais may be configured to receive feed from the feed delivery platform and distribute the feed to the insects. In some cases, the feed dais may be configured with various sensors, such as weight sensors, image components, light sensors, thermal sensors, etc., that may collect data related to the amount of feed associated with the dais and to signal a management module of the feed delivery platform to deliver feed when feed levels fall below a predetermined feed threshold or amount.

In this example, the facility may include racks of habitats, each having a feed dais located at approximately the same position with respect to the rack, such that a feed delivery platform may deliver feed to each habitat in a rack at substantially the same time.

In some implementations, the feed delivery platform may be an autonomous system configured to navigate the facility and to deliver feed to habitats. In some cases, the feed delivery platform may include wheels for traditional movement or balls for 360-degree steering. The feed delivery platform includes multiple sensors and types of sensors, such as light sensors, image components, motion sensors, proximity sensors, among others to assist with navigation and detecting obstructions in the feed delivery platform.

The feed delivery platform may also include one or more delivery apparatuses for supplying the habitats with feed. The delivery apparatuses may be an extendable plate, a conveyor, a feed tube, among others. The feed delivery platform may also include a hopper for housing feed that may be distributed to delivery apparatuses prior to supplying the habitats. Various chutes or tubes may be utilized to distribute the feed from the hopper to each of the delivery apparatuses. In some examples, sensors may be incorporated into the chute or tubes to count, measure, or identify an amount of feed being distributed to each of the delivery apparatuses for supplying the habitats.

In some cases, the amount of feed delivered to each delivery apparatus may vary or differ depending on the amount of feed remaining on each feed dais. For example, the feed delivery platform be equipped with sensors or imaging components that may collect data associated with each habitat. The feed delivery platform may analyze the image and/or sensor data to determine an amount of feed to deliver to the dais within the imaged habitat. Alternatively, the feed delivery platform may provide the image and sensor data to a remote management system that may determine the amount of feed to distribute to each habitat and provide the amount back to the delivery platform in response. The feed delivery platform may also receive the sensor and/or image data from the sensors incorporated into the feed chutes distributing the feed to the delivery apparatus. The chutes may also include valves or shutoff devices that the feed delivery platform may close when the feed delivery platform determines the appropriate amount of feed has been distributed to the appropriate feed delivery apparatus.

In some cases, the feed delivery platform may send the image or sensor data associated with each habitat to a management system for further processing. For example, the feed delivery platform or the management system may analyze the image and sensor data associated with each habitat to determine the health of the insects, the number of insects, if the insects are ready to move habitats, if the insects have matured to the next developmental stage, any issues with the habitat or insects, etc. For example, the delivery platform or the management system may be configured to notify or alert an administrator if an issue is detected.

In some implementations, the feed delivery platform may be configured to supply feed to two racks of habitats at substantially the same time. For example, the feed delivery platform may have feed delivery apparatuses on opposing sides of the feed delivery platform to, for instance, distribute feed to habitats on both sides of an aisle the feed delivery platform is traversing.

In some cases, the facility and/or the racks may include designations or markers that may be detected by sensors or image components mounted on the feed delivery platform. For example, markers may be placed in alignment with the racks on the floor of the facility. The feed delivery platforms may detect and orient themselves based on the floor markers prior to distributing feed to the habitats. Markers may also be placed on each habitat or on the racks, and the feed delivery platforms may detect and utilize the markers to orient themselves prior to distributing feed to the habitats.

In some implementations, the hopper may also include one or more sensors or image components to monitor a level or amount of feed within the hopper. If the feed delivery platform determines the feed falls below a first threshold amount, the feed delivery platform may be configured to navigate through the facility to a feed distribution station. The feed delivery platform may be configured to operate the feed distribution station to cause feed to be deposited into the hopper until the feed delivery platform determines that the feed in the hopper exceeds a second threshold. Once the feed in the hopper exceeds the second threshold, the feed delivery platform may resume feed distribution to the habitats.

In some cases, the feed delivery platform may monitor an existing battery life and if the battery life falls below a first power threshold, the feed delivery platform may navigate to a recharge station. The feed delivery platform may then resume feed delivery operations when the battery life exceeds a second power threshold.

In some cases, a facility may utilize multiple feed distribution platforms. Each of the platforms may be assigned to a region or area of the facility and may include different types or number of feed delivery apparatuses selected based on the type of insects and life stage of the insects within the habitats associated with the region or area.

FIG. 1 illustrates an example facility 100 having multiple racks 102 of insect habitats 104 and feed delivery platforms 106 for cultivating insects according to some implementations. In the illustrated example, each of the feed delivery platforms 106 may be configured to distribute feed to the habitats 104 along one or more of the paths 108. In some cases, the paths 108 may be predefined routes that are programmed into the feed delivery platforms 106. In other cases, the paths 108 may be assigned based on need by, for instance, a management system 110.

In still other cases, the paths 108 may be generated based on requests from various ones of the habitats 104. For example, each of the habitats 104 may be configured with sensors and/or image components that collect sensor and image data associated with the corresponding habitat. The sensor and/or image data may be provided to the management system 110 or processed by the habitats 104 to determine that the corresponding habitat 104 is low on feed and one of the feed delivery platforms 106 should be dispatched. Thus, the management system 110 or the feed delivery platform 106 receiving the requests may generate a path 108 for the feed delivery platform 106 including stops at habitats 104 requesting feed.

In other examples, the feed delivery platforms 106 may traverse the same path 108 each day at one or more predetermined times. In this example, the platforms 106 may stop at each habitat 104. The feed delivery platforms 106 or the habitats 104 may monitor a feed level of a feed dais associated with each habitat 104 to determine an amount of feed to distribute to each habitat 104. In this manner, each habitat 104 may receive feed at regular intervals but each habitat 104 does not necessarily receive the same amount of feed. For example, during the cultivating process, the population within each habitat 104 may vary and, thus, the amount of feed consumed within a period of time may also differ.

As the feed delivery platforms 106 approach a habitat 104, the feed delivery platforms 106 may detect a marker, such as marker 112, along the floor of the facility 100. For example, each of the racks 102 may be aligned with a marker, such as marker 112, along the floor of the facility, as shown in the illustrated example. In some cases, a particular marker, such as marker 112, may be placed between two adjacent racks 102 (e.g., two racks 102 on opposite sides of an aisle). The feed delivery platforms 106 may include sensors and image components along the front, back, side walls, bottom, or a combination thereof to detect the markers, such as marker 112. The feed delivery platforms 106 may analyze the sensor and/or image data collected by the various sensors and/or image components on the front, back, side walls, and/or bottom to detect the marker 112 and to orient the platform 106 in accordance with the marker 112. When the feed delivery platform 106 is properly aligned with the marker 112, the feed delivery platform 106 may distribute feed to each of the feed delivery apparatuses in accordance with an amount of feed for the corresponding habitat 104. Once the feed is distributed to the feed delivery apparatuses, the feed delivery apparatuses may then disperse to the feed to the habitats 104.

As the feed delivery platforms 106 traverse the paths 108 to distribute feed to the habitats 104, the feed delivery platform 106 may determine, via sensors and/or image components associated with a hopper carried by the feed delivery platforms 106, that the feed in the hopper falls below an empty threshold. The feed delivery platform 106 may stop distributing feed to the habitats 104 and proceed to navigate to a feed distribution station 114. The feed delivery platform 106 may be configured to operate the feed distribution station 114 to cause feed to be deposited into the hopper until the feed delivery platform 106 determines, via the sensor and/or image data associated with the hopper, that the feed in the hopper exceeds a full threshold. Once the feed in the hopper exceeds the full threshold, the feed delivery platform 106 may resume feed distribution to the habitats 104 by navigating to a location along the path 108 that the feed distribution platform 106 left off from.

Additionally, from time to time or upon the completion of a feed delivery operation or the path 108, the feed delivery platform 106 may determine that a battery or power level is below a low power threshold. The feed delivery platform 106 may stop distributing feed to the habitats 104 and proceed to navigate to a recharge area 116. The recharge station 116 may be configured to activate upon the detection of a feed delivery platform 106 or may be an inductive charging system that activates based on proximity of the feed delivery platform 106 to the recharge station 116. Once the feed delivery platform 106 determines the battery or power level has exceeded a recharge threshold, the feed delivery platform 106 may resume feed distribution to the habitats 104 by navigating to a location along the path 108 that the feed distribution platform 106 left off from. Alternatively, the feed delivery platform 106 may be configured to navigate to the feed distribution station 114 and refill the hopper prior to resuming normal feed delivery operations.

In the illustrated example, the feed distribution station 114 and the recharge stations 116 are located at designated areas within the facility 100. However, in some implementations, the facility 100 may include multiple feed distribution stations 114 and/or recharge stations 116 throughout the facility 100 to, for instance, reduce a distance between feed delivery platforms 106 and the stations 114 and 116 to reduce down time.

In the illustrated example, the management system 110 may be configured to coordinate the movement of the various feed delivery platforms 106. For example, the management system 110 may provide instructions to the feed delivery platforms 106 based on data received from the habitats 104. The management system 110 may also be configured to process the sensor and image data collected by the platforms 106 to reduce the overall cost of each of the feed delivery platforms 106. For instance, the management system 110 may receive image data associated with a habitat 104 and determine the amount of feed to dispense to the feed dais. The management system 110 may send the amount back to the feed delivery platform 106.

In other examples, the management system 110 may be configured to provide notifications or alerts to an operator or administrator of the facility 100 in response to identifying various issues associated with the operation of the habitats 104 or feed delivery platforms 106. For instance, the management system 110 may issue an alert if the sensor or image data indicates that an obstruction is located on the floor of the facility 100 blocking the progress of one or more of the feed delivery platforms 106 or if one of the habitats 104 has an unusual number of dead insects.

In some specific examples, the feed delivery platforms 106 may be configured to traverse the same path 108 at one or more times per day (e.g., at feeding time). In this example, the feed delivery platforms 106 may determine that a period of time has elapsed since a last feeding, fill the hopper at the feed station 114, traverse the assigned path 108, deliver feed to the habitats 104 along the path 108, and return to the recharge station 116. The feed delivery platforms 106 may then wait a second period of time prior to starting another feed distribution run. In some cases, the first period of time and the second period of time may be the same. In other cases, the first period of time and the second period of time may vary. For example, the first period of time may be 12 hours or overnight and the second period of time may be 6 hours or a period between breakfast and lunch.

Figure 2:
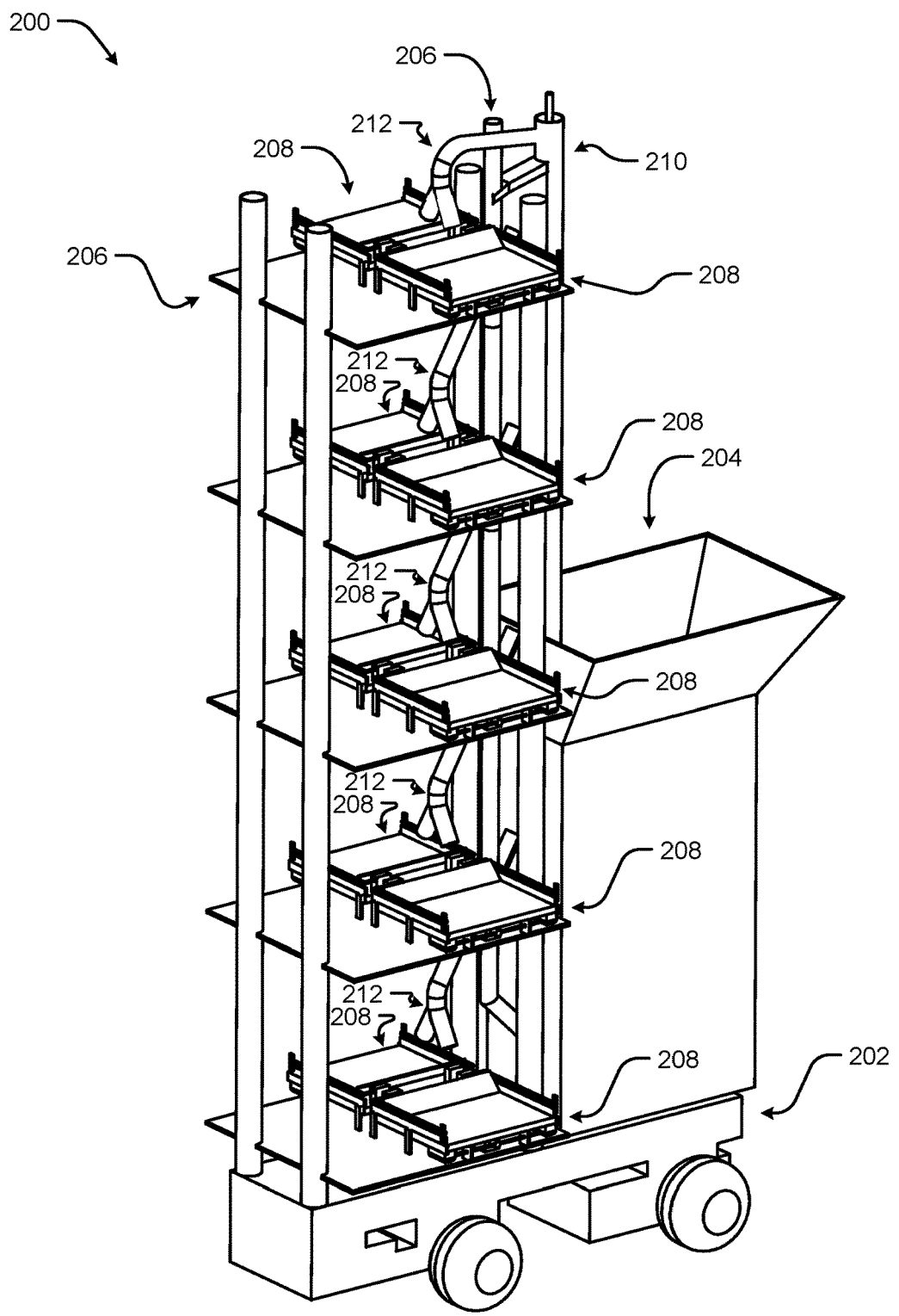
FIG. 2 illustrates an example feed delivery platform in navigation mode according to some implementations.

FIG. 2 illustrates an example feed delivery platform 200 in navigation mode according to some implementations. The feed delivery platform 200 may include a base 202 equipped with a hopper 204 and a feed delivery apparatus support tower 206. The feed delivery apparatus support tower 206 may include multiple levels each including one or more feed delivery apparatuses 208 for delivering the feed into the habitats. A feed distribution tube 210 may be configured to transfer feed from the hopper 204 to each of the feed delivery apparatuses 208.

The feed delivery apparatus support tower 206 may be formed from various materials including PVC, copper, aluminum, stainless steel, wood, titanium, various alloys, as well as combinations thereof. In the illustrated example, the feed delivery apparatus support tower 206 may include any number of levels or tiers each including one or more of the feed delivery apparatuses 208. In some cases, the number of levels may correspond to a number of levels utilized in the rack system housing the habitats. For example, if the rack system in a facility houses five levels of habitats then the feed delivery apparatus support tower 206 may include five levels of feed delivery apparatuses 208, such that the feed delivery platform 200 may dispense feed to a habitat on each level of the rack at substantially the same time.

In the illustrated example, each level of the feed delivery apparatus support tower 206 includes two opposing feed delivery apparatuses 208. Each of the opposing feed delivery apparatuses 208 are configured to face opposite directions, such that feed may be delivered to habitats on both sides of an aisle. In other words, the feed delivery platform 200 may deliver feed to multiple habitats housed on two different racks, as will be discussed in more detail below.

Each of the feed delivery apparatuses 208 may receive an amount of feed from the hopper 204 via the feed distribution tube 210 and various feed distribution chutes 212. The feed distribution chutes 212 may be equipped with sensors that may count the number or amount of feed being distributed to each try and to open and close one or more valves to control the amount of feed dispensed onto each of the feed delivery apparatuses 208, as will be discussed in more detail below. Once the feed is distributed to each of the feed delivery apparatuses 208, the feed delivery apparatuses 208 may actuate and deposit the feed into a corresponding habitat, as illustrated below with respect to FIG. 3.

Figure 3:
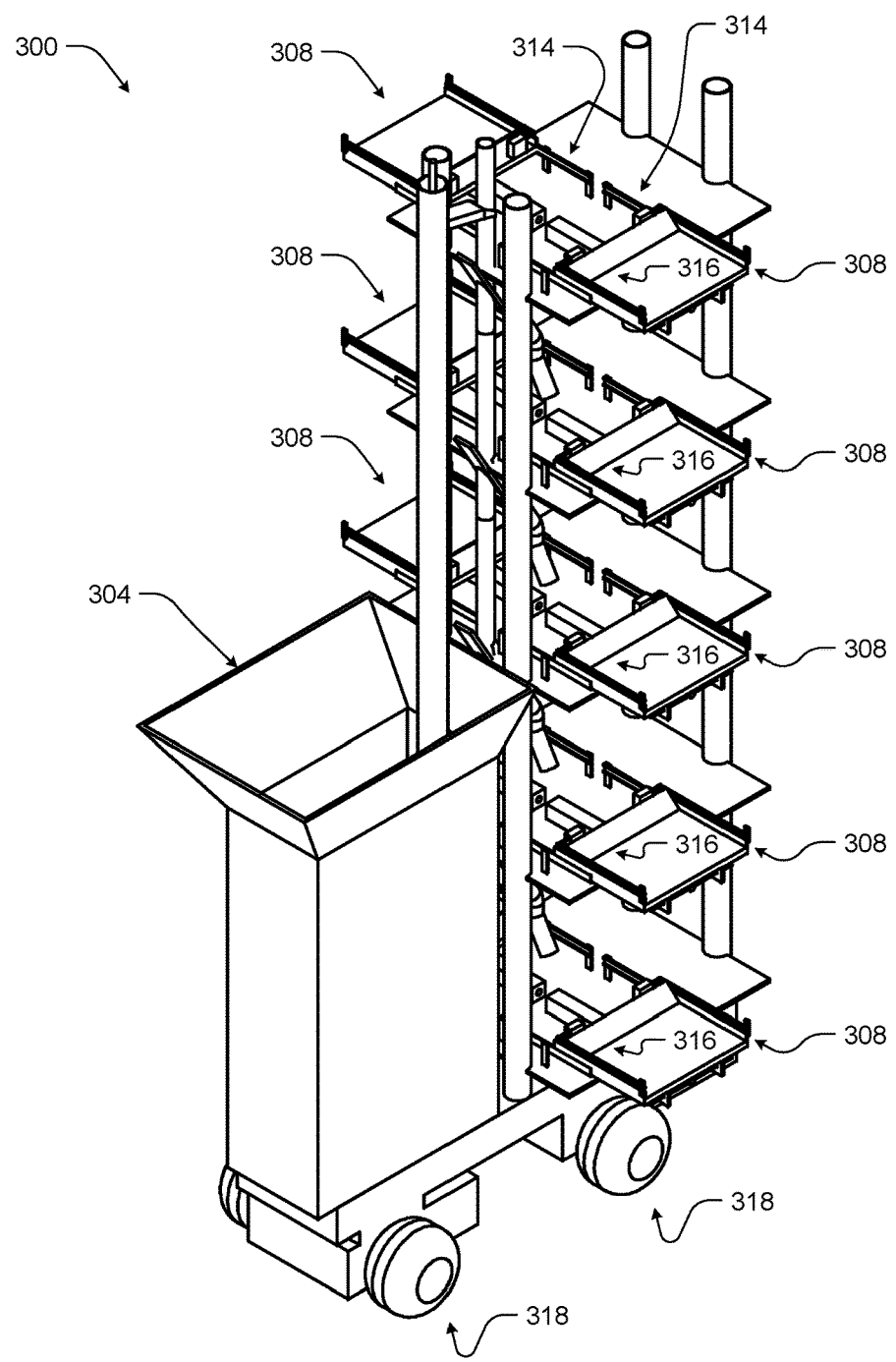
FIG. 3 illustrates an example feed delivery platform in a feed distribution mode according to some implementations.

FIG. 3 illustrates an example feed delivery platform 300 in a feed distribution mode according to some implementations. For instance, in the illustrated example, the feed delivery apparatuses 308 have extended via tracks, such as tracks 314. Thus, in the illustrated example, the feed delivery apparatuses 308 may be extending over an edge of a corresponding habitat within a rack, as discussed above with respect to FIG. 1.

For example, once feed is distributed to each of the feed delivery apparatuses 308 via the chutes discussed above with respect to FIG. 2, the feed delivery apparatuses 308 may extend over the habitats. Once the feed delivery apparatuses 308 have extended, a distribution device, such as distribution devices 316, may push the feed on the feed delivery apparatuses 308 onto the dais within each habitat, as illustrated with respect to FIGS. 12 and 13.

As described above, the feed delivery platform 300 may be configured to navigate throughout a facility to deliver the feed to the habitats. In some cases, the feed delivery platform 300 may include various types of conveying devices, such as wheels 318. Alternatively, the conveying devices may include tracks or guide based systems, ball and socket systems (e.g., for 360-degree navigation or turning), treads or continuous track devices, among others.

Figure 4:
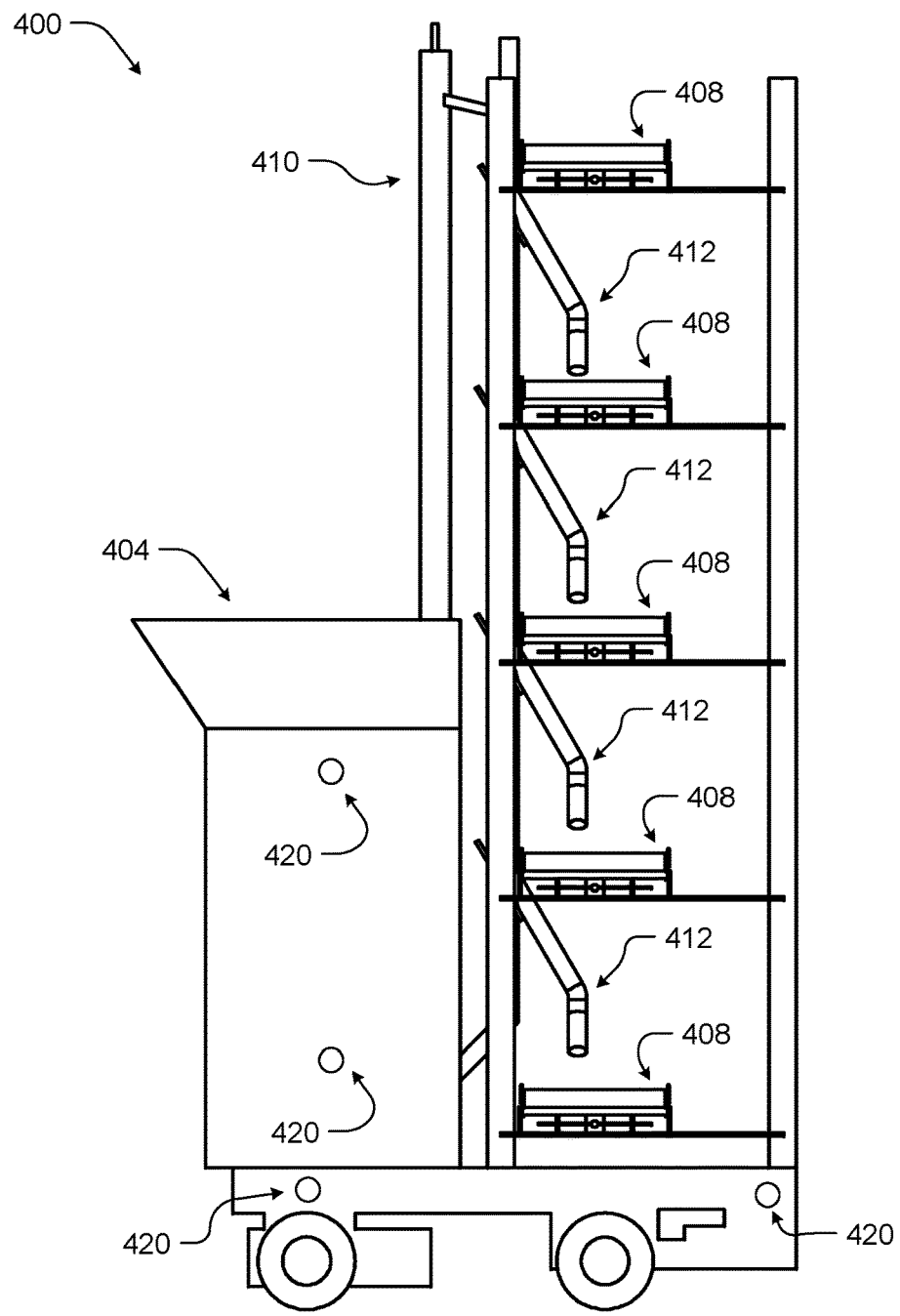
FIG. 4 illustrates a side-view of the example feed delivery platform of FIGS. 2 and 3 according to some implementations.

FIG. 4 illustrates a side-view of the example feed delivery platform 400 of FIGS. 2 and 3 according to some implementations. In the illustrated example, the feed delivery platform 400 includes a hopper 404 and feed distribution tube 410 for supplying feed to the feed delivery apparatuses 408 via the corresponding feed distribution chutes 412, as discussed above.

Additionally, as described above with respect to FIG. 1, the feed delivery platform 400 may be configured to navigate throughout a facility to deliver the feed to the habitats. In the illustrated example, the feed delivery platform 400 includes multiple sensors and/or image components 420 on the walls of the platform 400. The sensors may collect data associated with the position of the feed delivery platform 400, obstructions along the navigation path, and/or the position of the racks and/or habitats. In the illustrated example, the sensors and/or image components 420 are shown on the side of the platform 400, however, the sensors 420 may be on the side, front, and rear of the feed delivery platform 400. In some cases, the sensors and/or image components 420 may include thermal sensors, light sensors, three-dimensional cameras, infrared cameras, red-green-blue cameras, depth sensors, proximity sensors, motion sensors, gyroscopes, accelerometers, inertial measurement devices, etc.

The collected data may be provided to a navigation module stored within the feed delivery platform 400 and may be utilized to adjust the position and/or course of the platform 400 as the feed delivery platform 400 delivers feed to the habitat. For example, a fuzzy logic system may be utilized to provide course correction based on the collected data received.

Figure 5:
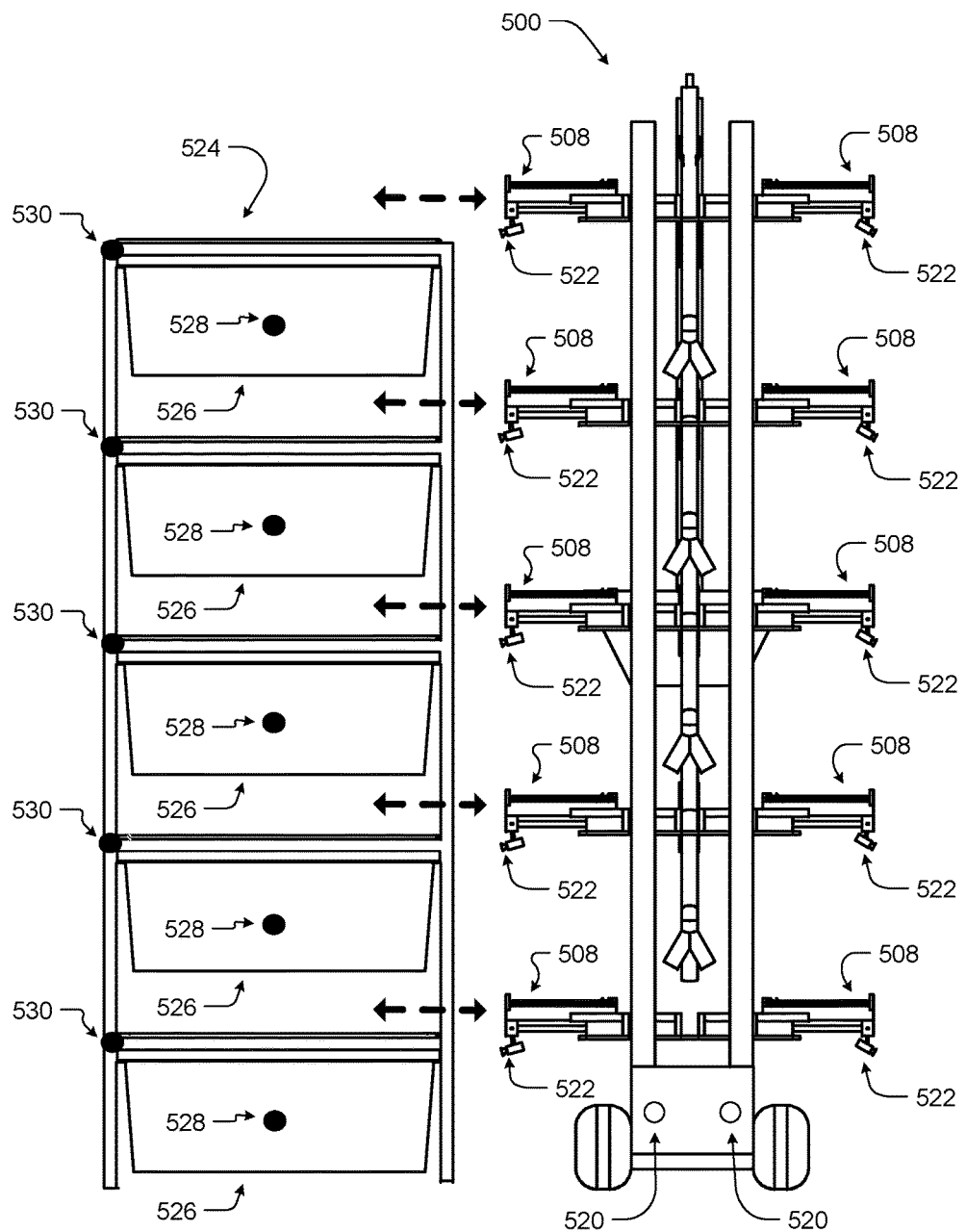
FIG. 5 illustrates a front-view of the example feed delivery platform of FIGS. 2 and 3 engaging a rack of habitats for feed distribution according to some implementations.

FIG. 5 illustrates a front-view of the example feed delivery platform 500 of FIGS. 2 and 3 engaging a rack 524 of habitats 526 for feed distribution according to some implementations. In the illustrated example, feed delivery apparatuses 508 are in the process of extending over the habitats 526. An image component or sensor 522 may be associated with each of the feed delivery apparatuses 508. The image components 522 may collect data associated with each of the habitats 526. For example, the image data collected by the image components 522 may be analyzed to identify a number of insects within the habitat 522 to determine a health of the population, to determine the amount of feed to distribute into the habitat 526 by each of the feed delivery apparatuses 508, to assist with aligning the feed delivery apparatuses 508 with the feed daises in the habitats 522, as well as other issues associated with the habitat 522 or the insects within the habitat 522.

In some examples, the feed delivery platform 500 may orient with the rack 524 or the habitats 526 prior to extending the feed delivery apparatuses 508 as shown. In some cases, the habitats 526 may include markers 528 that may be detected by sensors or image components, such as image components 522 or the sensors 520, on the platform 500 and utilized by the feed delivery platform 500 to achieve a substantially appropriate alignment with the habitats 526 prior to distributing the feed. Similarly, the rack 524 may also include markers 530 that may also be detected by sensors or image components, such as image components 522 or the sensors 520, on the platform 500 and utilized by the feed delivery platform 500 to achieve the substantially appropriate alignment with the habitats 526 prior to distributing the feed.

Figure 6:
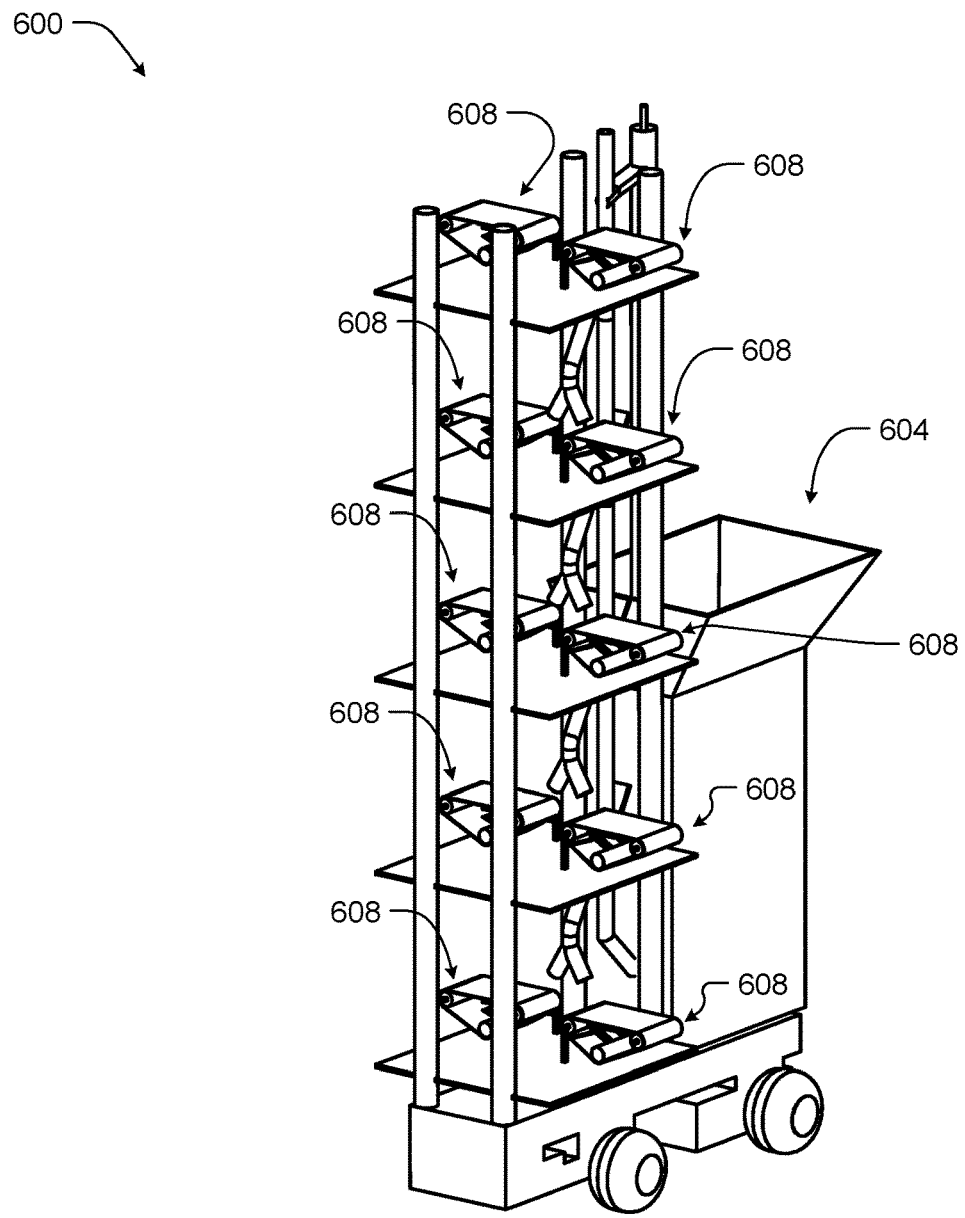
FIG. 6 illustrates another example feed delivery platform according to some implementations.

FIG. 6 illustrates another example feed delivery platform 600 according to some implementations. The feed delivery platform 600 is similar to the feed delivery platforms 200-500 described above. However, the feed delivery platform 600 includes conveyor based feed delivery apparatuses 608 in lieu of the apparatuses 208, 308, 408, and 508 described above. In the illustrated example, the conveyor based feed delivery apparatuses 608 may be configured to extend over the habitats when the feed delivery platform 600 is oriented with the racks for feed distribution. In other cases, the conveyor based feed delivery apparatuses 608 may be mounted on tracks, such as the tracks 314 of FIG. 3, to extend the conveyor based feed delivery apparatuses 608 over the edge of the habitats.

In some cases, the conveyor based feed delivery apparatuses 608 may distribute the feed to the habitats as the feed is received via the feed delivery chutes (not shown). In some cases, the conveyor based feed delivery apparatuses 608 may include a pressure sensor that may cause the conveyor based feed delivery apparatuses 608 to enable when feed is present on the belt and to disable otherwise.

Figure 7:
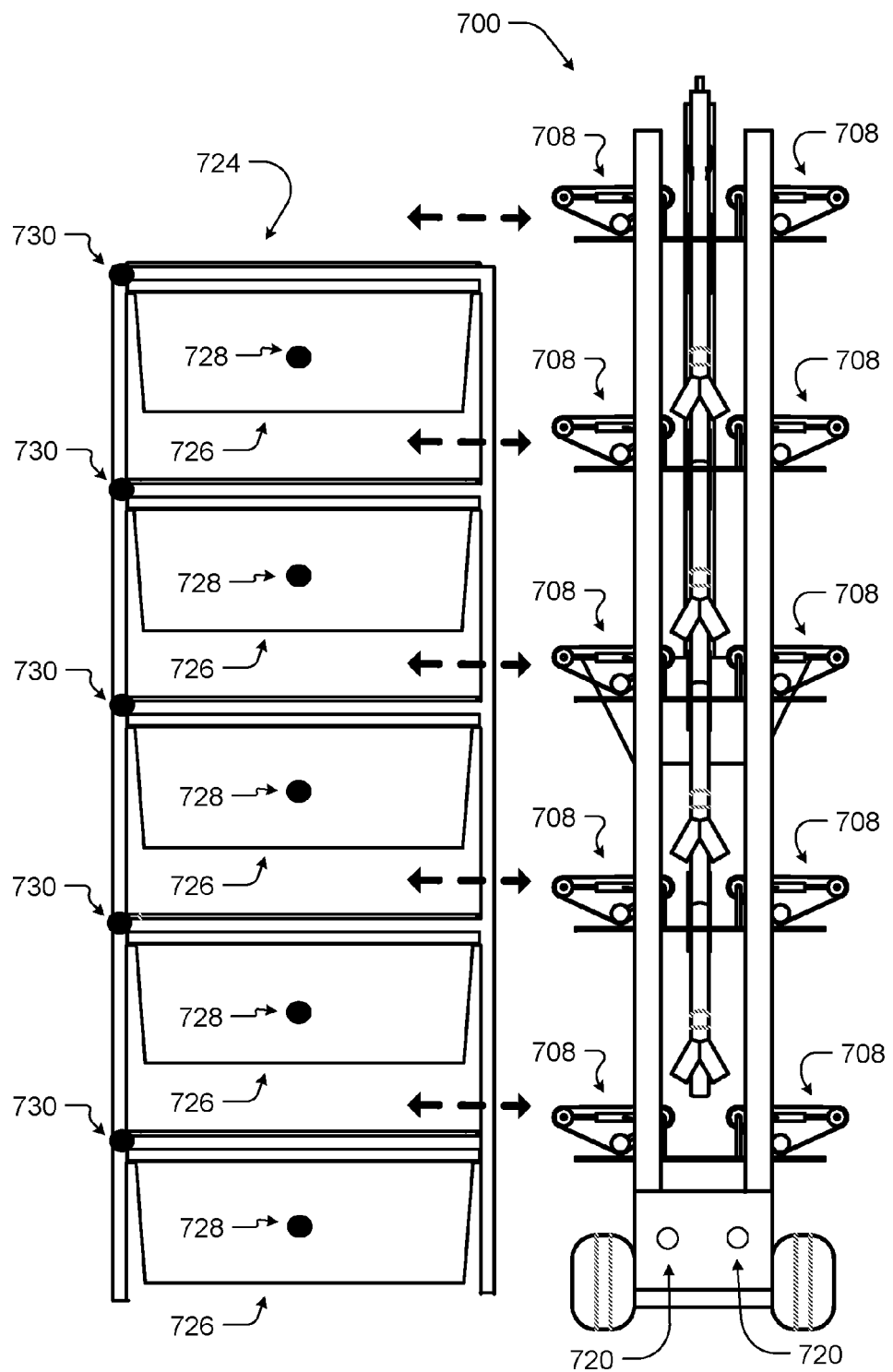
FIG. 7 illustrates a side-view of the feed delivery platform of FIG. 6 according to some implementations.

FIG. 7 illustrates a side-view of the feed delivery platform 700 of FIG. 6 according to some implementations. In the illustrated example, conveyor based feed delivery apparatuses 708 are in the process of distributing feed to the habitats 726. As described above, in some examples, the feed delivery platform 700 may orient with the rack 724 or the habitats 726 prior to enabling the conveyor based feed delivery apparatuses 708 as shown. In some cases, the habitats 726 may include markers 728 that may be detected by sensors or image components, such the sensors 720 used to navigate the platform 700, on the feed delivery platform 700. The markers 728 may be utilized by the feed delivery platform 700 to achieve a substantially appropriate alignment with the habitats 726 prior to distributing the feed. Similarly, the rack 724 may also include markers 730 that may also be detected by sensors or image components, such the sensors 720, on the platform 700. The markers 730 may also be utilized by the feed delivery platform 700 to achieve the substantially appropriate alignment with the habitats 726 prior to distributing the feed.

Figure 8:
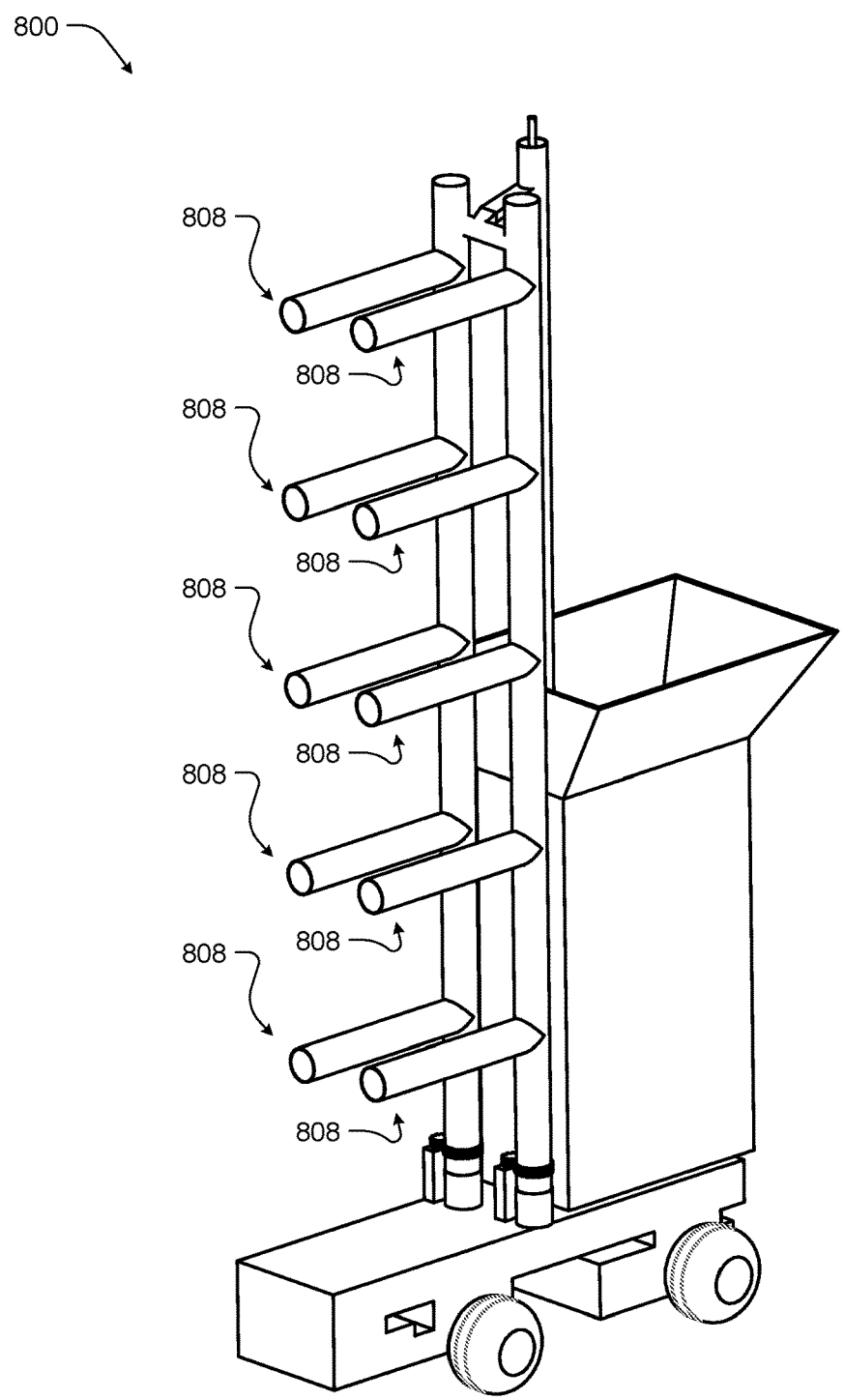
FIG. 8 illustrates yet another example feed delivery platform according to some implementations.

FIG. 8 illustrates yet another example feed delivery platform 800 according to some implementations. The feed delivery platform 800 is similar to the feed delivery platforms 200-700 described above. However, the feed delivery platform 800 includes chute based feed delivery apparatuses 808 in lieu of the apparatuses 208, 308, 408, 508, 608, and 708 described above. In the illustrated example, the chute based feed delivery apparatuses 808 may be configured to swing out over the habitats as a boom arm when the feed delivery platform 800 is oriented with the racks for feed distribution.

In some cases, the chute based feed delivery apparatuses 808 may distribute the feed to the habitats as the feed is received via the feed delivery chutes (not shown), for example, by acting as an extension of the feed delivery chutes. In some cases, the chute based feed delivery apparatuses 808 may include a sensor that may cause the chute based feed delivery apparatuses 808 to open or close a shutoff valve or door in response to distributing a predefined amount of feed.

Figure 9:
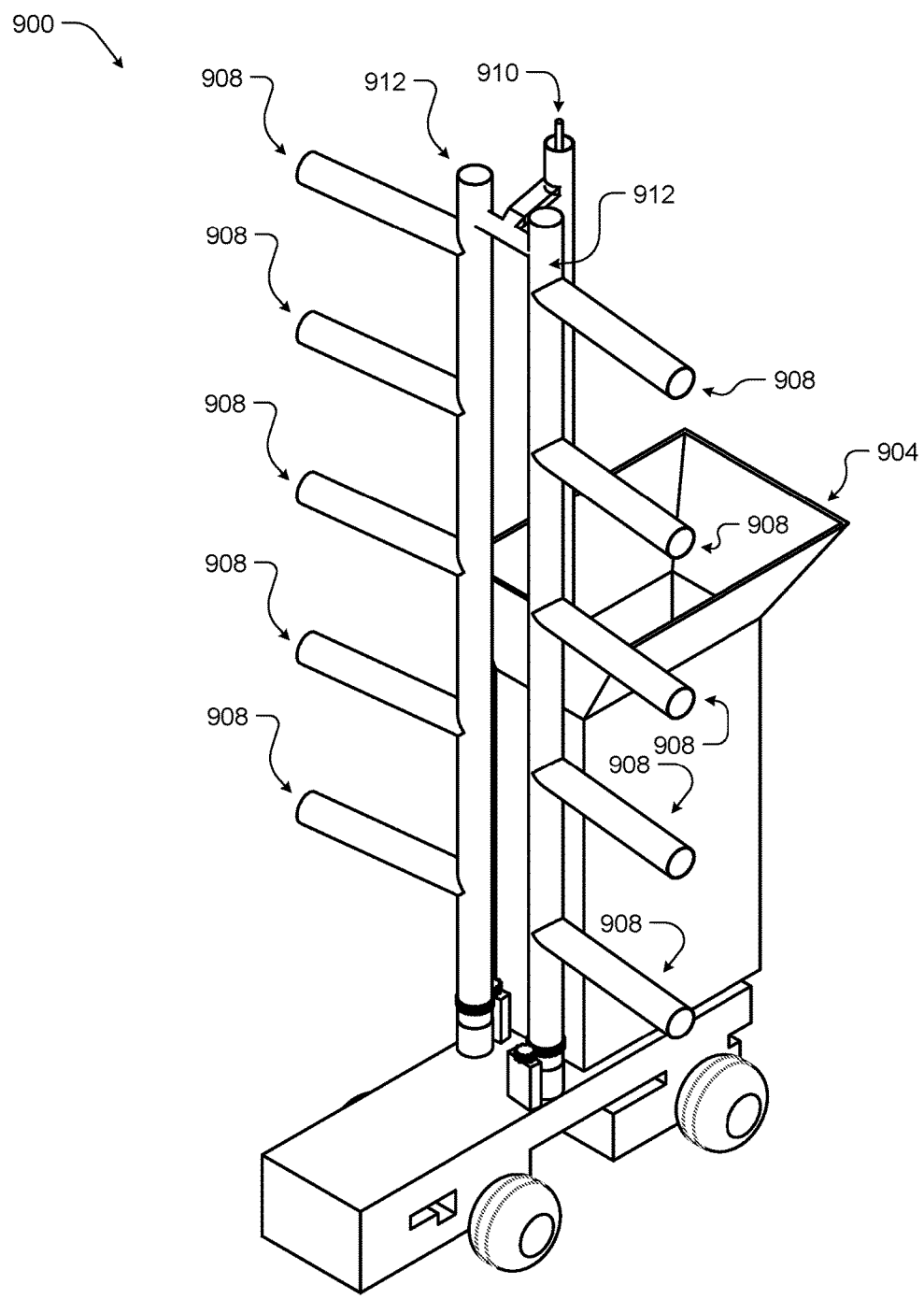
FIG. 9 illustrates a perspective view of the feed delivery platform of FIG. 8 according to some implementations.

FIG. 9 illustrates a perspective view of the feed delivery platform 900 of FIG. 8 according to some implementations. In the illustrated example, chute based feed delivery apparatuses 908 are in the distribution mode with the arms extended. As described above, in some examples, the feed delivery platform 900 may orient with the racks and the habitats. The feed delivery platform 900 may then extend the chute based feed delivery apparatuses 908, as shown. The feed distribution tube 910 may then supply feed from the hopper 904 to the chute based feed delivery apparatuses 908 via the feed distribution chutes 912. The chute based feed delivery apparatuses 908 may each deposit the feed onto a dais within each habitat.

Figure 10:
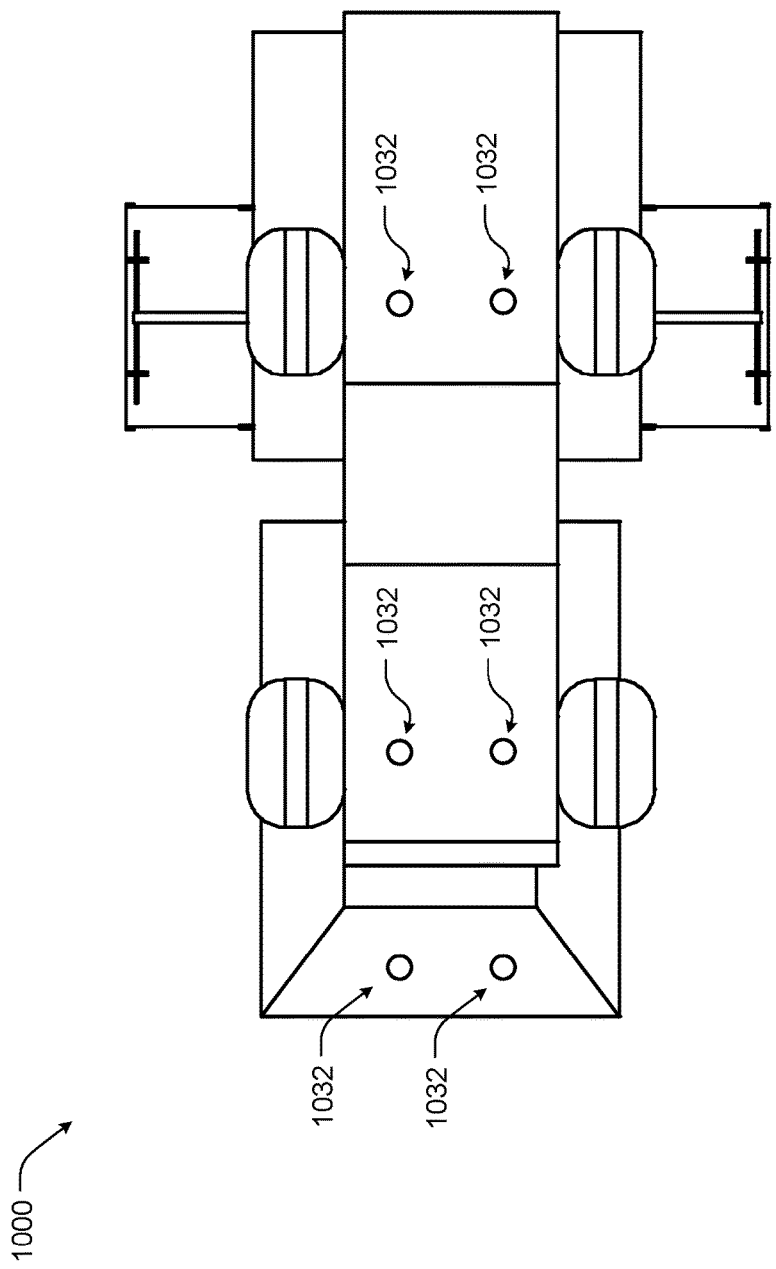
FIG. 10 illustrates a bottom view of the example feed delivery platform of FIGS. 2-9 according to some implementations.

FIG. 10 illustrates a bottom view of the example feed delivery platform 1000 of FIGS. 2-9 according to some implementations. As discussed above, the feed delivery platforms 1000 may include navigation sensors or image components positioned on the walls of the feed delivery platforms. In the illustrated example, the feed delivery platform 1000 may also include sensors or image components 1032 along the bottom of the platform 1000. The sensors 1032 may assist with navigation and/or identify markers on the floor of a facility, as described above with respect to FIG. 1, to assist the feed delivery platform 1000 with orienting with respect to the habitats prior to distributing feed. In some cases, the sensors 1032 may include thermal sensors, light sensors, three-dimensional cameras, infrared cameras, red-green-blue cameras, depth sensors, proximity sensors, motion sensors, gyroscopes, accelerometers, inertial measurement devices, etc.

Figure 11:
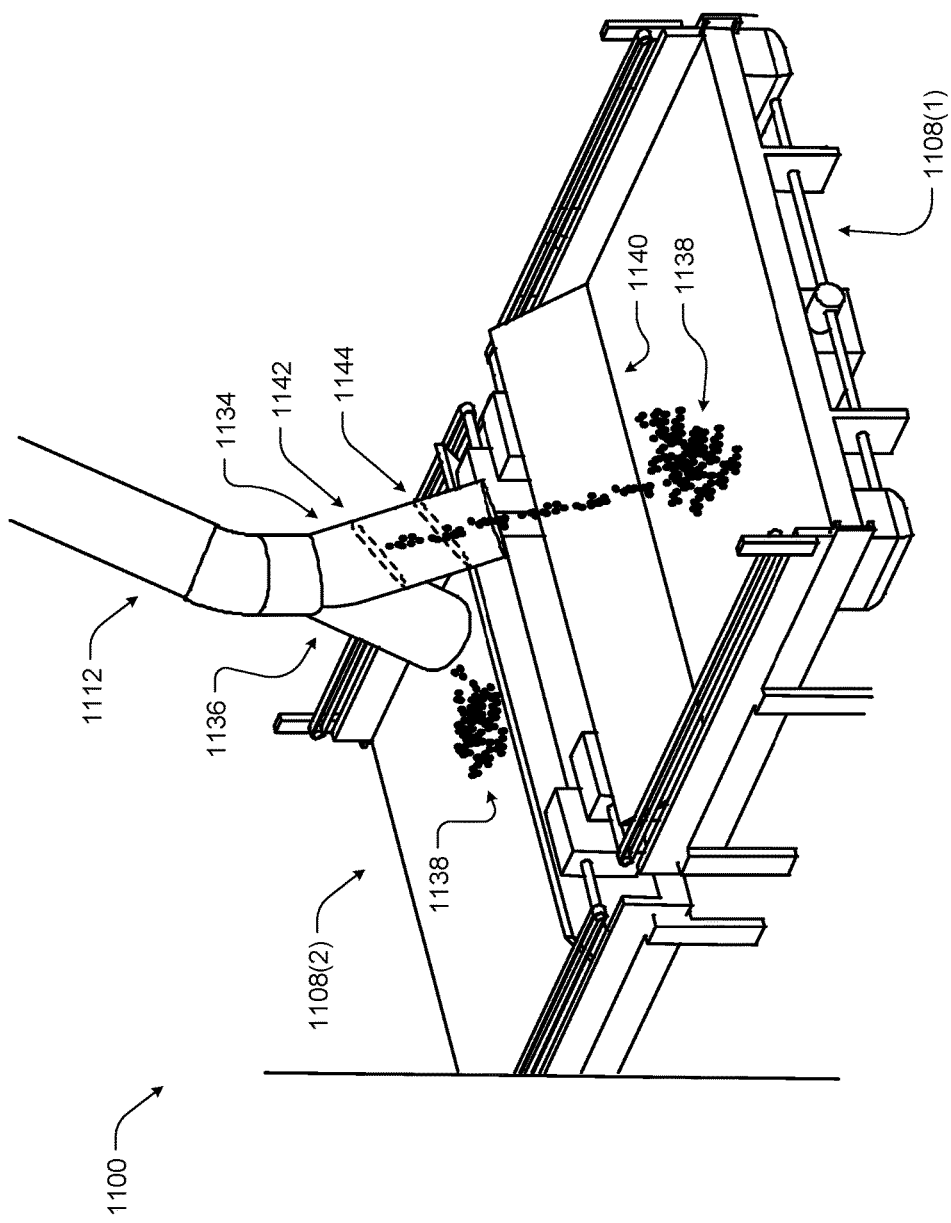
FIG. 11 illustrates an example of feed delivery apparatuses and a chute of a feed delivery platform according to some implementations.

FIG. 11 illustrates an example of feed delivery apparatuses 1108(1) and 1108(2) and a chute 1112 of a feed delivery platform 1100 according to some implementations. The chute 1112 includes a first path 1134 and a second path 1136. The first path 1134 is configured to deliver feed 1138 to the feed delivery apparatus 1108(1) and the second path 1136 is configured to deliver feed 1138 to the feed delivery apparatus 1108(2). Each of the feed delivery apparatuses 1108(1) and 1108(2) also include a delivery device, such as delivery device 1140 of feed delivery apparatus 1108(1), to push or distribute the feed 1138 into the habitats once the feed 1138 has been dispensed onto the feed delivery apparatuses 1108(1) and 1108(2).

In the illustrated example, the chute 1112 is delivering feed 1134 to the feed delivery apparatuses 1108(1) and 1108(2). As the feed 1134 is delivered to the feed delivery apparatus 1108(1), the feed 1134 may pass through one or more sensors or image components, such as sensors 1142 and 1144. In one example, the sensors 1142 and 1144 may be motion sensors that are configured to detect an amount of feed passing through the first path 1134 of the chute 1112. In some cases, as the amount of feed 1134 exceeds a first feed threshold associated with the feed delivery apparatus 1108(1) the first path 1134 of the chute 1112 may be shut off to prevent further distribution of feed. For example, an end cap may close the opening of the first path 1134. In other cases, a valve associated with the joint of the chute 1112 between the first path 1134 and the second path 1136 may close to allow feed 1138 to continue to be distributed to the second delivery apparatus 1108(2) but prevent feed 1138 from being distributed onto the first delivery apparatus 1108(1) in excess of the first feed threshold.

As described above, in some cases, the first feed threshold may vary depending on the population of the habitat receiving the feed 1138, an amount of feed 1138 remaining un-eaten in the habitat receiving the feed 1138, a time of day, a date or season, life stage of the insects in the habitat receiving the feed 1138, etc. Additionally, while the first feed threshold may be associated with the first feed delivery apparatus 1108(1), a second feed threshold may be associated with the second delivery apparatus 1108(2) and the second feed threshold may differ from the first feed threshold. It should be understood, that if the feed delivery platform 1100 includes other feed delivery apparatuses, each of the additional feed delivery apparatus may include an associated threshold.

Figure 12:
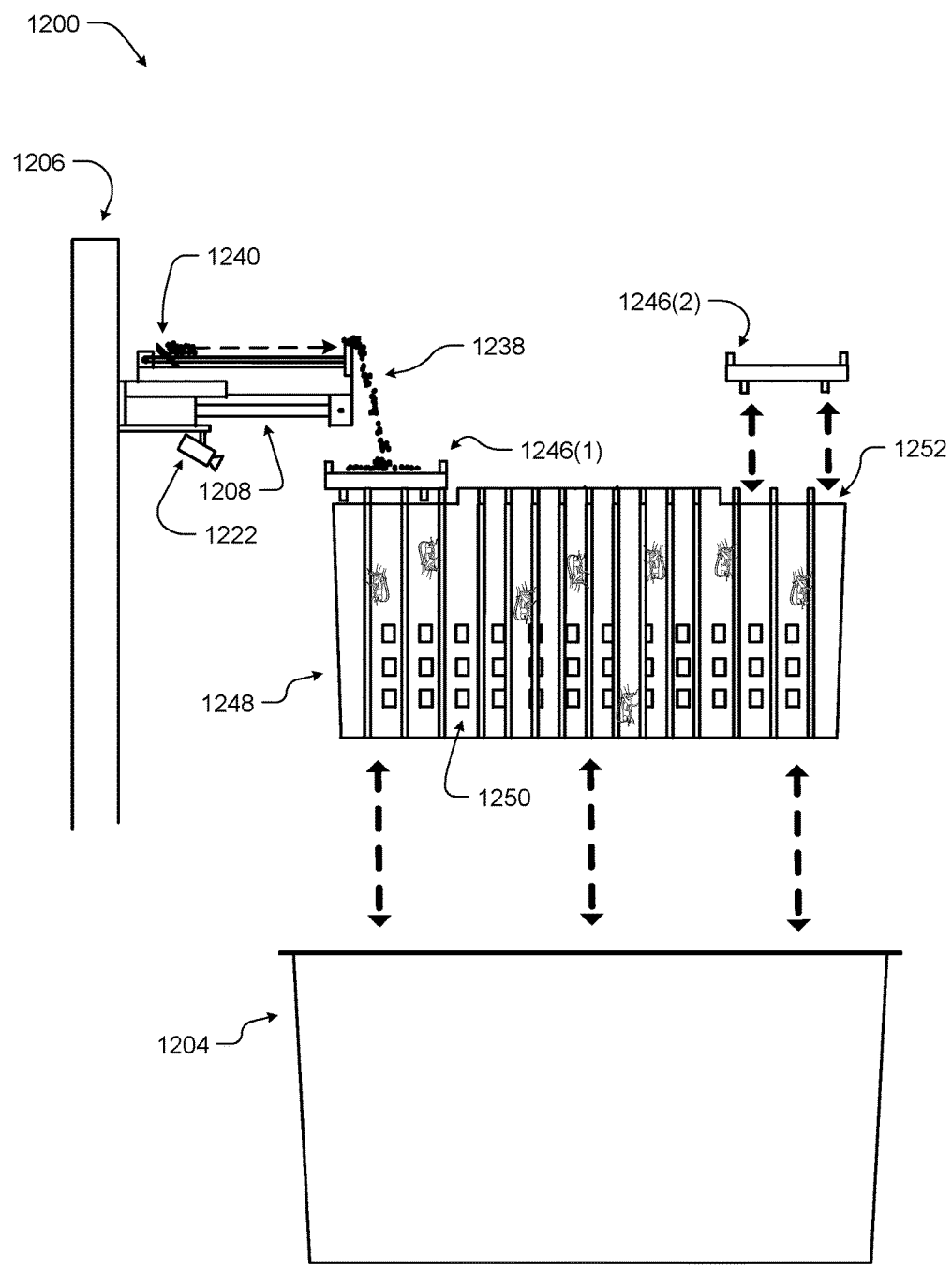
FIG. 12 illustrates an example of a feed delivery platform distributing feed to a habitat according to some implementations.

FIG. 12 illustrates an example of a feed delivery platform 1200 distributing feed 1238 to a habitat 1204 according to some implementations. In the illustrated example, a feed delivery apparatus 1208 is distributing the feed 1238 onto a first feed dais 1246(1) associated with the habitat 1204. The habitat 1204 includes a habitat insert 1248 currently shown as removed from the habitat 1204. The insert 1248 may be included in the habitat 1204 to increase the overall total surface area within the same volume previously contained within the habitat 1204, as the increase in surface area results in a corresponding increase in the insects that may be cultivated within the same volume of space. In the illustrated example, the insert 1248 may generally form a grid, helix or cross-section within the interior space of the habitat 1204. As shown in the illustrated example, the insert 1248 may be removable from the habitat 1204 and include vertical walls that allow the insert 1248 to be shaken to be dislodged or removed from the habitat 1204 during harvesting in a more efficient manner. For example, the insert 1248 may be moved over a collection bin and vibrated to cause the insects to fall off of or detach from the surfaces of the insert 1248. The insert 1248 may also include perforations 1250 along the interior walls to increase airflow and insect mobility throughout the entire volume and allow the insects to more easily reach the feed dais 1246(1).

In the current example, the insert 1248 is configured to receive the first feed dais 1246(1) as well as a second feed dais 1246(2) shown removed from the insert 1248. For example, the daises 1246(1) and 1246(2) may be removable for cleaning prior to or following the harvesting of the insects. In some cases, the feed daises 1246(1) and 1246(2) may be positioned at predetermined locations within the habitat 1204, for instance, by including a depressed region 1252 on the top surface of the insert 1248. Thus, the daises 1246(1) and 1246(2) may be configured to receive feed 1238 from the feed delivery platform 1208 and distribute the feed 1238 to the insects. In some cases, the feed daises 1246(1) and 1246(2) may be configured with various sensors, such as weight sensors, image components, light sensors, thermal sensors, etc., that may collect data related to the amount of feed 1138 remaining on the daises 1246(1) and 1246(2) and that signal a management module or the feed delivery platform 1200 to deliver feed 1238 when feed levels on either of the daises 1246(1) and 1246(2) or a total amount of feed 1138 on both of the daises 1246(1) and 1246(2) falls below a predetermined feed threshold or amount. In some cases, the data collected by the daises 1246(1) and 1246(2) may be utilized by the feed delivery platform 1200 to determine the amount of feed 1138 to distribute to the habitat 1204.

In the current example, the feed delivery apparatus 1208 is connected to a support tower 1206 and has received an amount of feed 1238 from a hopper of the feed delivery platform 1200 via a feed tube (not shown) and a feed chute (not shown) as described above. The amount of feed 1238 may be based on a population of the habitat 1204, an amount of feed 1138 remaining un-eaten in the habitat 1204, a time of day, a date or season, life stage of the insects in the habitat 1204, etc. In this example, a feed delivery device 1240 pushes or moves the feed 1238 forward off of the feed delivery apparatus 1208 and onto the first feed dais 1246(1), where the feed 1238 may be consumed by the insects in the habitat 1204.

Figure 13:
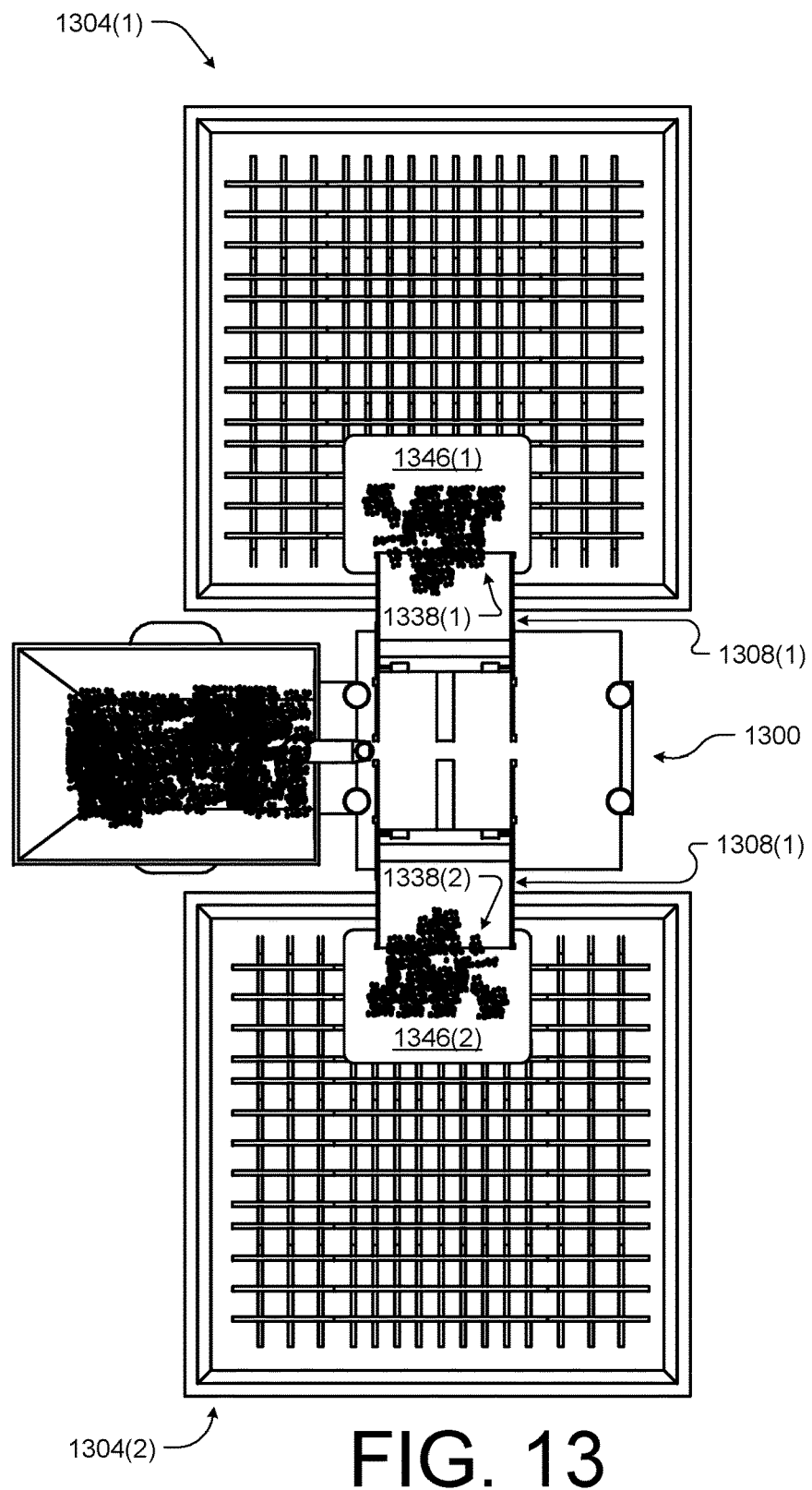
FIG. 13 illustrates another example feed delivery platform distributing feed to habitats according to some implementations.

FIG. 13 illustrates another example feed delivery platform 1300 distributing feed to habitats 1304(1) and 1304(2) according to some implementations. Similar to FIG. 12 above, in the current example, a feed delivery apparatus 1308(1) has received a first amount of feed 1338(1) based on an amount of feed desired in habitat 1304(1) and a feed delivery apparatus 1308(2) has received a second amount of feed 1338(2) based on an amount of feed desired in habitat 1304(2). The first amount of feed 1338(1) and the second amount of feed 1338(2) may be based on a population of the corresponding habitat 1304(1) and 1304(2), an amount of feed remaining un-eaten in the corresponding habitat 1304(1) and 1304(2), a time of day, a date or season, life stage of the insects in the corresponding habitat 1304(1) and 1304(2), an amount requested by the corresponding habitat 1304(1) and 1304(2), among others. As described above, in some cases, the first amount of feed 1338(1) may vary from the second amount of feed 1338(2) to meet the needs of the individual populations of insects within each of the habitats 1304(1) and 1304(2).

As shown, the feed delivery platform 1300 is capable of distributing feed 1338 to multiple racks of habitats 1304 on opposing sides of an aisle within an insect cultivating facility. By distributing to multiple racks at substantially the same time the overall costs and time associated with feed delivery may be reduced within the facility.

FIGS. 14 through 17 provide example flow diagrams illustrating example processes for implementing the feed delivery systems described above. The processes are illustrated as a collection of blocks in a logical flow diagram, which represent a sequence of operations, some or all of which can be implemented in hardware, software or a combination thereof. In the context of software, the blocks represent computer-executable instructions stored on one or more computer-readable media that, which when executed by one or more processors, perform the recited operations. Generally, computer-executable instructions include routines, programs, objects, components, data structures and the like that perform particular functions or implement particular abstract data types.

The order in which the operations are described should not be construed as a limitation. Any number of the described blocks can be combined in any order and/or in parallel to implement the process, or alternative processes, and not all of the blocks need be executed. For discussion purposes, the processes herein are described with reference to the frameworks, architectures and environments described in the examples herein, although the processes may be implemented in a wide variety of other frameworks, architectures or environments.

Figure 14:
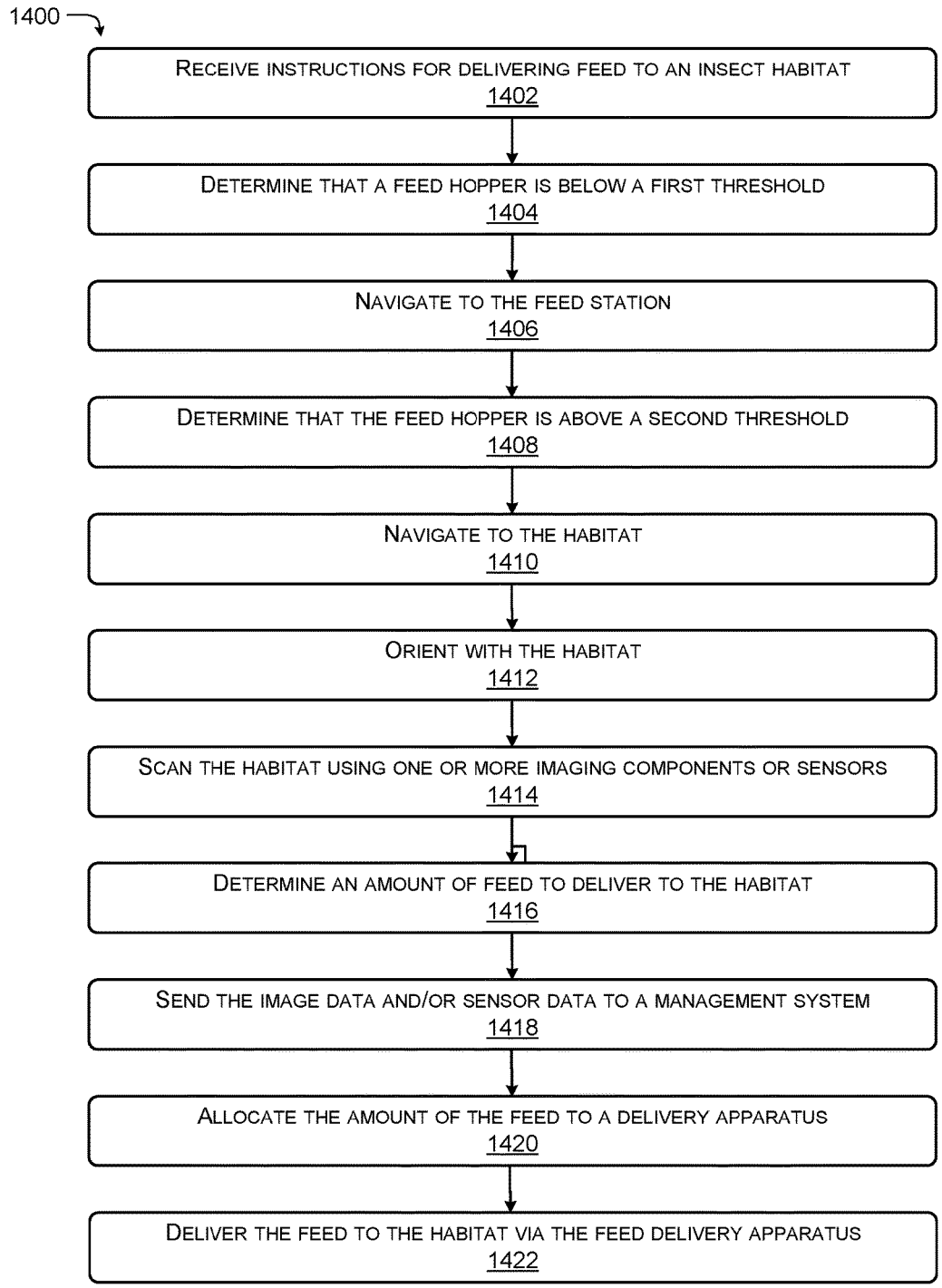
FIG. 14 illustrates an example flow diagram showing an illustrative process associated with the feed delivery platform according to some implementations.

FIG. 14 illustrates an example flow diagram showing an illustrative process 1400 associated with the feed delivery platform according to some implementations. As described above, insects may be cultivated in habitats arranged on three-dimensional racks within a facility. Each of the habitats requires regular feeding and the amount of feed to be delivered to each habitat may differ based on, for instance, population within each habitat, life stage of the insects, feeding schedules, types of insects in the habitat. In some implementations, a feed delivery platform may be configured to navigate to a rack or habitat, determine an amount of feed to distribute to one or more habitats, and dispense the feed to the habitats without the need for human interaction.

At 1402, a feed delivery platform may receive instructions to deliver feed to a habitat. For example, the feed delivery platform may receive a request from the habitat to delivery feed. In other cases, the instructions may be provided by a management system that receives data associated with each habitat in a facility and coordinates the delivery of feed, water, lighting, waste removal, etc. with respect to the habitats within the facility. In other examples, the feed delivery platform may initiate a feed distribution operation based on an external or internal trigger, such as a time of day, the elapsing of a period of time, a battery or amount of stored power exceeding a threshold, among others.

At 1404, the feed delivery platform may determine the feed hopper is below a first threshold. For example, a sensor or image component may collect data associated with the hopper and the data may be utilized to determine if the feed in the hopper is below the first threshold. The sensors may include light sensors, weight sensors, proximity sensors, etc. For instance, in one particular case, the feed within the hopper may fall below the feed threshold when a weight associated with the feed falls below a weight threshold.

At 1406, the feed delivery platform may navigate to the feed station and initiate a hopper refill process. For example, the feed station may be configured to distribute a predetermined amount of feed into the hopper based on detecting the presence of the feed delivery platform within or on the feed station. In other cases, the feed delivery platform may send a wireless signal to notify the feed station that the feed delivery platform is properly positioned and ready to receive feed into the hopper.

At 1408, the feed delivery platform or the feed station may determine the feed within the hopper has exceeded a second threshold. For example, when the feed in the hopper is over a predetermined amount or weight, the feed delivery platform may send a second wireless signal to the feed station to cease filling the hopper. In other examples, the feed station may include a weight sensor below the feed delivery platform so that the feed station can stop filling the hopper when the combined weight of the platform and the feed exceeds a limit.

At 1410, the feed delivery platform may navigate to the habitat. In some cases, the feed delivery platform may follow a defined path. In other cases, the feed delivery platform may receive navigation instructions and/or paths from the management system based on, for instance, a known location of other feed delivery platforms. In one particular implementation, the feed delivery platform may navigate to the habitat using sensors and image components mounted on the outside of the platform and an image processing module together with a processor to determine obstacles and to guide the platform between rows of habitats.

At 1412, the feed delivery platform may orient with the habitat prior to dispensing the feed. For example, the facility may include markers or identifiers, such as but not limited to barcodes, QR codes, taped/painted lines or magnetic strips, on the floor that the platform may detect and utilize to orient prior to distributing the feed. In other cases, as described above, markers may be located on the habitats or the racks holding the habitats to further assist with orienting the platform prior to dispensing the feed.

At 1414, the feed delivery platform may scan the habitat using one or more sensors or imaging components. For example, the feed delivery platform may include imaging components mounted on the feed delivery apparatuses that may image each of the habitats that feed may be delivered to, based on the current position and orientation of the platform. In some cases, the image data collected may be used to determine a health of the insect population, a stage of development, time until harvesting or ready to harvest, and/or an amount of feed remaining within the habitat, as will be discussed below.

At 1416, the feed delivery platform determines an amount of feed to distribute the habitat. For example, based on the image or sensor data collected at 1414, the feed delivery platform may determine a population of insects within the habitat and an amount of feed remaining on the dais. Based on the population, the amount of feed on the dais, and an expected feed consumption rate of the insects, the platform may determine the amount of feed to distribute.

At 1418, the feed delivery platform may send the image data and/or sensor data to the management system. For example, the management system may receive, from the platform the image data and/or sensor data, and process the image or sensor data collected at 1414 to determine the amount of feed to distribute and send the amount back to the delivery platform. In other cases, the management system may utilize the image data and/or sensor data to determine other aspects associated with the habitat, such as insect size, insect health, habitat cleanliness, foreign objects, debris, pests, insect life stage, insect type, feed distribution or consumption, insect distribution within a habitat, weight of the population, weight or amount of the reaming feed, conditions of the insert, dais, or habitat, temperature, lighting level, etc.

At 1420, the feed delivery platform allocates the amount of feed to a feed delivery apparatus corresponding to the habitat. For example, the feed may be supplied to the feed delivery apparatus via a feed tube or chute from a feed hopper. The feed chute may monitor an amount of feed being dispensed onto the feed delivery apparatus. The chute may continue to dispense feed until a threshold amount of feed (e.g., the amount determined at 1416) is met or exceeded. Once the threshold amount of feed is reached the chute may disable or close to prevent further feed from being distributed onto the feed delivery apparatus. In this manner, if the platform has multiple feed delivery apparatuses, the chute may control the amount of feed delivered to each delivery apparatus individually.

At 1422, the feed delivery platform delivers the feed to the habitat via the feed delivery apparatus. For example, the feed delivery apparatus may be extended via a track or guide over the edge of the habitat. Once extended, an arm may push or move the feed over the edge of the feed delivery apparatus and onto a dais within the habitat. In another example, the feed may dispense out of a second tube or chute. In yet another example, the feed may be moved via a conveyor into the habitat.

Figure 15:
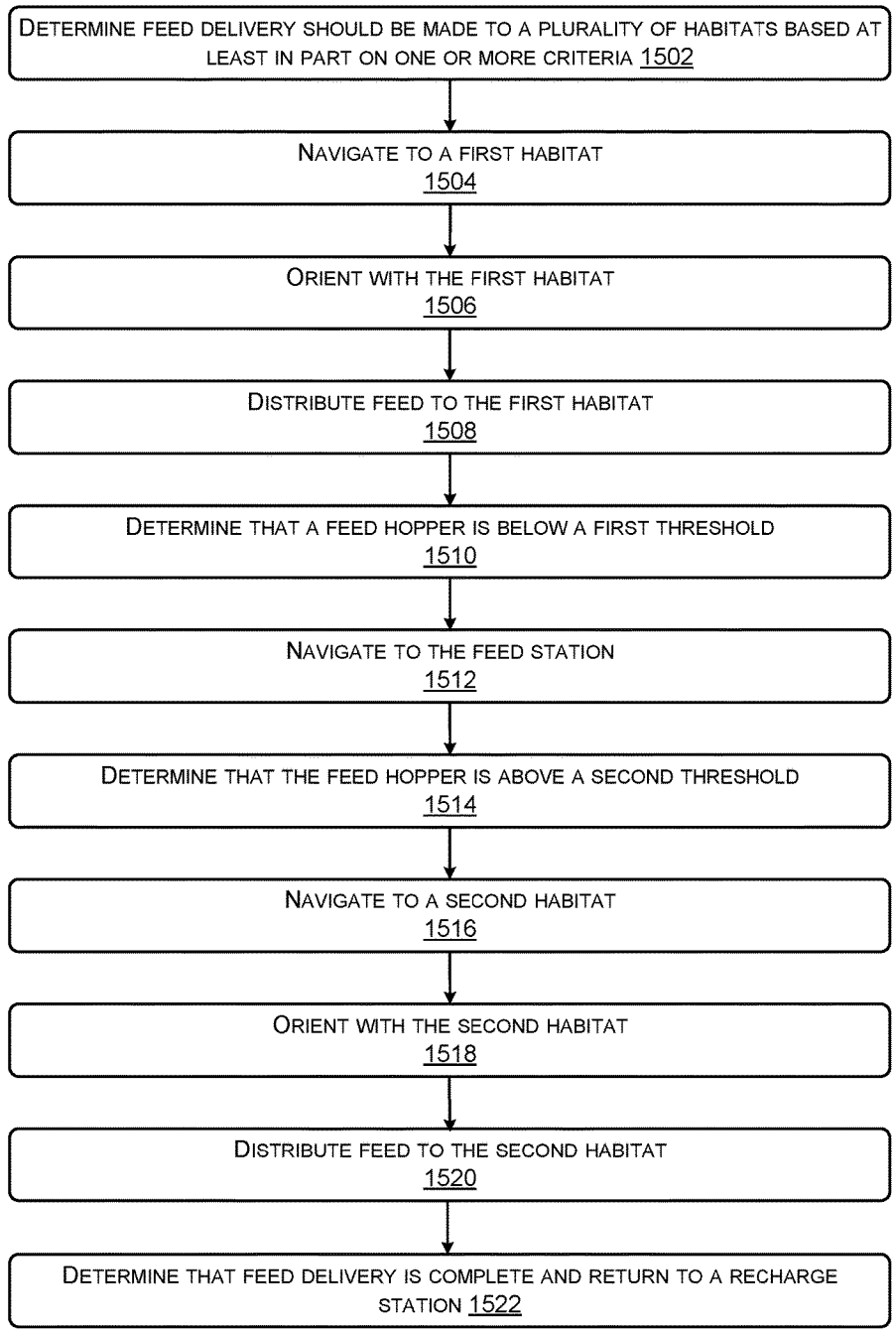
FIG. 15 illustrates another example flow diagram showing an illustrative process associated with the feed delivery platform according to some implementations.

FIG. 15 illustrates another example flow diagram showing an illustrative process 1500 associated with the feed delivery platform according to some implementations. As described above, insects may be cultivated in habitats arranged on three-dimensional racks within a facility. Each of the habitats requires regular feeding and the amount of feed to be delivered to each habitat may differ based on, for instance, population within each habitat, life stage of the insects, feeding schedules, types of insects in the habitat. In some implementation, a feed delivery platform may be configured to navigate to a rack or habitat, determine an amount of feed to distribute to one or more habitats, and dispense the feed to the habitats without the need for human interaction.

At 1502, the feed delivery platform determines that feed delivery should be made to a plurality of habitats based, at least in part, on one or more criteria. For example, the criteria may include one or more of a time of day, a timer expiring, a signal from a management system, a signal from one or more habitats, an analysis of data received from a habitat (for example, the weight of feed on a feed dais falling below a threshold), among others.

At 1504, the feed delivery platform may navigate to a first habitat. In some cases, the feed delivery platform may follow a defined path. In other cases, the feed delivery platform may receive navigation instructions and/or paths from the management system based on, for instance, a known location of other feed delivery platforms. In one particular implementation, the feed delivery platform may navigate to the first habitat using sensors and image components mounted on the outside of the platform and an image processing module together with a processor to determine obstacles and to guide the platform between rows of habitats.

At 1506, the feed delivery platform may orient with the first habitat prior to dispensing the feed. For example, the facility may include markers or identifiers, such as but not limited to barcodes, QR codes, painted/tape lines or magnetic markers on the floor that the platform may detect and utilize to orient prior to distributing the feed. In other cases, as described above, markers may be located on the first habitat or the racks holding the first habitat to further assist with orienting the platform prior to dispensing the feed.

At 1508, the feed delivery platform delivers the feed to the first habitat. For example, the feed delivery platform allocates the amount of feed to a feed delivery apparatus corresponding to the first habitat. In some cases, the feed may be supplied to the feed delivery apparatus via a feed tube or chute from a feed hopper. Once the feed is distributed, the feed delivery apparatus may be extended via a track or guide over the edge of the first habitat and an arm may push or move the feed over the edge of the feed delivery apparatus and onto a dais within the first habitat.

At 1510, the feed delivery platform may determine that the feed within a feed hopper is below a first threshold. For example, the feed hopper may be equipped with a weight sensor that may monitor a weight associated with the first feed. In other examples, the hopper may be equipped with proximity sensors positioned at a level on the walls within the hopper associated with the first threshold (e.g., when the feed level drops below the level of the proximity sensors the sensors trigger).

At 1512, the feed delivery platform may navigate to the feed station and initiate a hopper refill process. For example, the feed station may be configured to distribute a predetermined amount of feed into the hopper based on detecting the presence of the feed delivery platform within or on the feed station. In other cases, the feed delivery platform may send a wireless signal to notify the feed station that the feed delivery platform is properly positioned and ready to receive feed into the hopper.

At 1514, the feed delivery platform or the feed station may determine the feed within the hopper has exceeded a second threshold. For example, when the feed in the hopper is over a predetermined amount or weight, the feed delivery platform may send a second wireless signal to the feed station to cease filling the hopper. In other examples, the feed station may include a weight sensor below the feed delivery platform and stop filling the hopper when the combined weight of the platform and the feed exceeds a limit.

At 1516, the feed delivery platform may navigate to a second habitat. For example, the feed delivery platform may deliver feed to habitats on multiple racks within the facility and refill the hopper as necessary during the feed delivery process. In some cases, the feed delivery platform may return to a position on the defined path at which the feed delivery platform left off and then proceed to the second habitat.

At 1518, the feed delivery platform may orient with the second habitat prior to dispensing the feed. As discussed above, the facility may include markers or identifiers, such as but not limited to barcodes, QR codes, taped/painted lines or magnetic markers, on the floor that the platform may detect and utilize to orient prior to distributing the feed. Additionally, markers may be located on the second habitat or the racks holding the second habitat to further assist with orienting the platform prior to dispensing the feed.

At 1520, the feed delivery platform delivers the feed to the second habitat. For example, the feed delivery platform allocates the amount of feed to a feed delivery apparatus corresponding to the second habitat. In some cases, the amount allocated may differ from the amount allocated to the first habitat based on the requirements of each specific habitat. As discussed above, the feed may be supplied to the feed delivery apparatus via a feed tube or chute from a feed hopper. Once the feed is distributed, the feed delivery apparatus may be extended via a track or guide over the edge of the second habitat and an arm may push or move the feed over the edge of the feed delivery apparatus and onto a dais within the second habitat.

At 1522, the feed delivery platform may determine that the feed delivery is complete and return to a recharge station. For example, the feed delivery platform may be configured to return to a recharge platform following each feed delivery. In some cases, the recharge station may also be a waiting area at which the feed delivery platform remains until another feed delivery is initiated.

Figure 16:
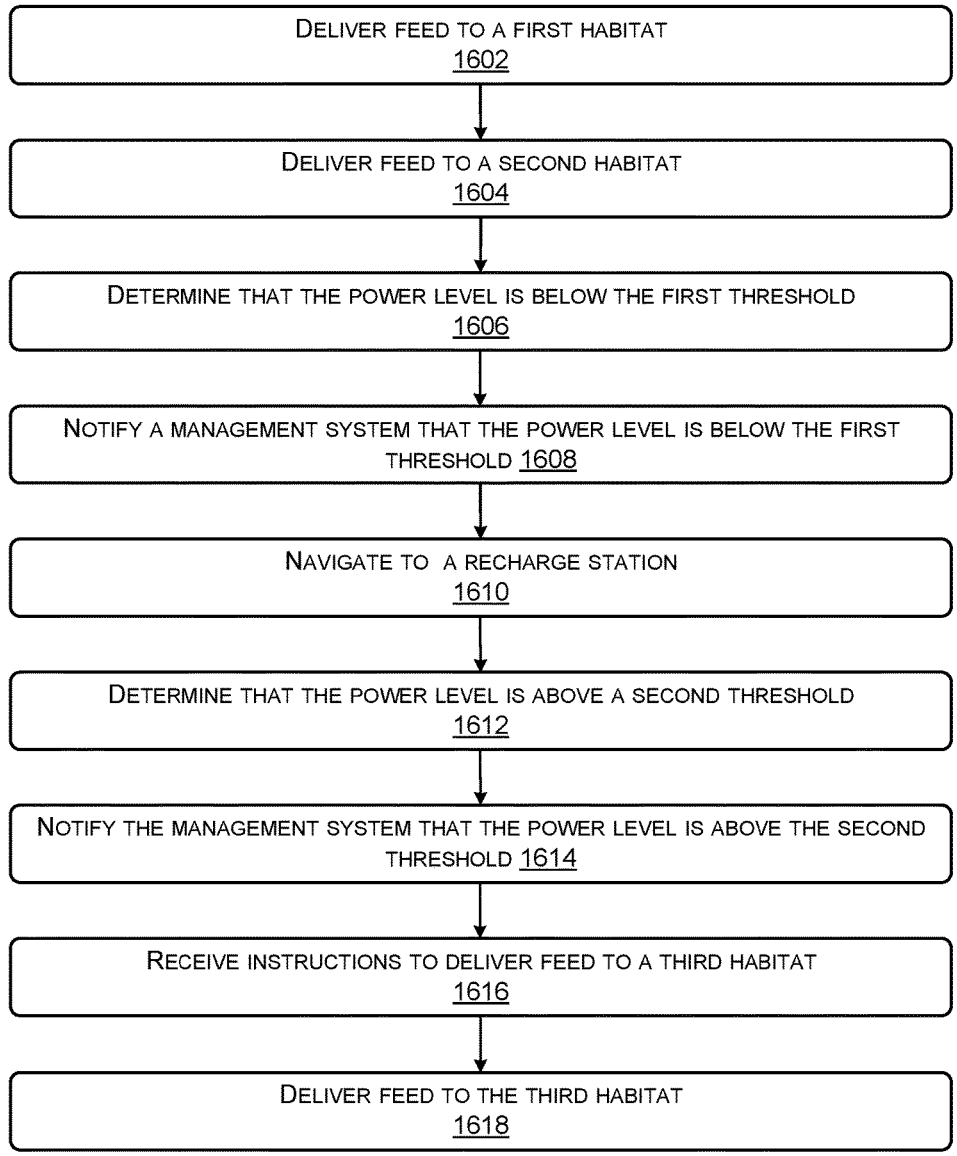
FIG. 16 illustrates yet another example flow diagram showing an illustrative process associated with the feed delivery platform according to some implementations.

FIG. 16 illustrates yet another example flow diagram showing an illustrative process 1600 associated with the feed delivery platform according to some implementations. As described above, insects may be cultivated in habitats arranged on three-dimensional racks within a facility. Each of the habitats requires regular feeding and the amount of feed to be delivered to each habitat may differ based on, for instance, population within each habitat, life stage of the insects, feeding schedules, types of insects in the habitat. In some implementations, a feed delivery platform may be configured to navigate to a rack or habitat, determine an amount of feed to distribute to one or more habitats, and dispense the feed to the habitats without the need for human interaction. From time to time, the feed delivery platforms may benefit from a recharge during a feed delivery and return to a recharge station, as described below.

At 1602, the feed delivery platform delivers the feed to a first habitat. For example, the feed delivery platform may navigate or drive to a position adjacent to the first habitat, orient with the first habitat, and dispense the feed to the first habitat via a feed delivery apparatus.

At 1604, the feed delivery platform delivers the feed to a second habitat. For example, the feed delivery platform may again navigate or drive to a position adjacent to the second habitat, orient with the second habitat, and dispense the feed to the second habitat via the feed delivery apparatus. In some examples, the feed delivery apparatus that delivered the feed to the first habitat may differ from the feed delivery apparatus that delivered feed to the second habitat.

At 1606, the feed delivery platform determines that the power level is below a first threshold (e.g., a low power threshold). For example, the feed delivery platform may monitor a power storage level, a current output, and/or a voltage output associated with a battery or other power source of the feed delivery platform and identify if the stored power, the current, and/or the voltage falls below a corresponding threshold (e.g., a power level threshold, a current threshold, or a voltage threshold).

At 1608, the feed delivery platform may notify the management system that the power level is below the first threshold. For example, the feed delivery platform may notify the management system such that a second feed delivery platform may be dispatched to continue or complete the current feed delivery. Additionally, the feed delivery platform may notify the management system so that the management system may assign a recharge station to the feed delivery platform or provide additional navigation paths to assist the feed delivery platform in returning to a recharge station.

At 1610, the feed delivery platform may navigate to the recharge station. In some cases, the feed delivery platform may follow a defined path. In other cases, the feed delivery platform may receive navigation instructions and/or paths from the management system based on, for instance, a known location of other feed delivery platforms. In one particular implementation, the feed delivery platform may navigate to the recharge station using sensors and image components mounted on the outside of the platform and an image processing module together with a processor to determine obstacles and to guide the platform between rows of habitats.

At 1612, the feed delivery platform may determine that the power level is above a second threshold (e.g., the power source is recharged). For example, the feed delivery platform may monitor a power storage level, a current output, and/or a voltage output associated with a battery or other power source of the feed delivery platform and identify if the stored power, the current, and/or the voltage has returned to a normal level (e.g., a normal power level threshold, a normal current threshold, or a normal voltage threshold).

At 1614, the feed delivery platform may notify the management system that the power level is above the second threshold. For example, the feed delivery platform may notify the management system to receive additional instructions to begin or resume a feed delivery. Alternately, the feed delivery platform may be configured to resume the feed delivery from the location at which the feed delivery platform left off.

At 1616, the feed delivery platform may receive instructions to deliver feed to a third habitat from the management system. For example, the management system may have one or more lists of habitats that require feeding and assign the next available habitat or the closest habitat on the list to the feed delivery platform.

At 618, the feed delivery platform delivers the feed to the third habitat. For example, the feed delivery platform may again navigate or drive to a position adjacent to the third habitat, orient with the third habitat, and dispense the feed to the third habitat via the feed delivery apparatus.

Figure 17:
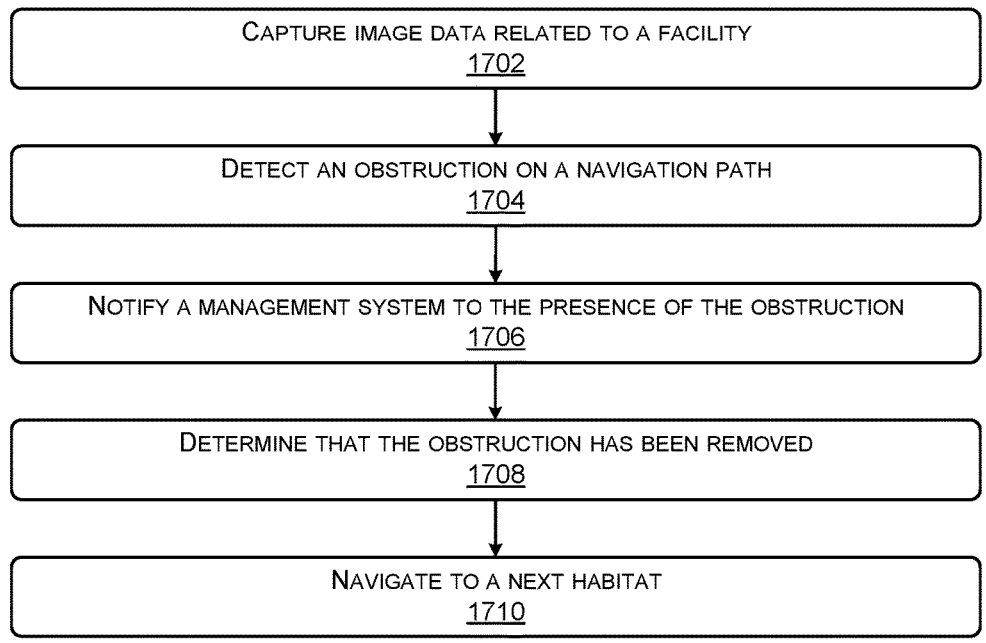
FIG. 17 illustrates still another example flow diagram showing an illustrative process associated with the feed delivery platform according to some implementations.

FIG. 17 illustrates still another example flow diagram showing an illustrative process 1700 associated with the feed delivery platform according to some implementations. As described above, insects may be cultivated in habitats arranged on three-dimensional racks within a facility. Each of the habitats requires regular feeding and the amount of feed to be delivered to each habitat may differ based on, for instance, population within each habitat, life stage of the insects, feeding schedules, types of insects in the habitat. In some implementations, a feed delivery platform may be configured to capture image and/or sensor data associated with the facility and/or each of the habitats. The feed delivery platform may utilize the image data to assist with navigation, as well as to provide the data to the management system for monitoring the health and status of the facility or each habitat.

At 1702, a feed delivery platform captures image or sensor data related to a facility. For example, the image and/or sensor data may be collected with respect to each habitat as the feed delivery platform distributes feed and with respect to the facility as the feed delivery platform navigates from rack of habitats to rack of habitats.

At 1704, the feed delivery platform may detect an obstruction in the navigation path. For example, a habitat may have fallen off a rack into an aisle way and be blocking the feed delivery platform's path.

At 1706, the feed delivery platform may notify a management system to the presence of the obstruction. For example, the feed delivery platform may provide the management system the image or sensor data collected. In another example, the feed delivery platform may report the obstruction and a location within the facility at which the obstruction may be located, such that the management system may dispatch an operator or an autonomous vehicle to remove the obstruction from the facility floor.

At 1708, the feed delivery platform may determine that the obstruction has been removed. In some cases, the feed delivery platform may go into a low power or sleep state upon identifying the obstruction and resume activity when the feed delivery platform receives a signal from the management system. In other cases, the feed delivery may identify by analyzing the image and/or sensor data that the obstruction has been removed.

At 1710, the feed delivery platform resumes the feed delivery and navigates to a next habitat or rack of habitats. For example, the feed delivery platform may navigate or drive to a position adjacent to the next habitat, orient with the next habitat, and dispense the feed to the next habitat via the feed delivery apparatus.

Figure 18:
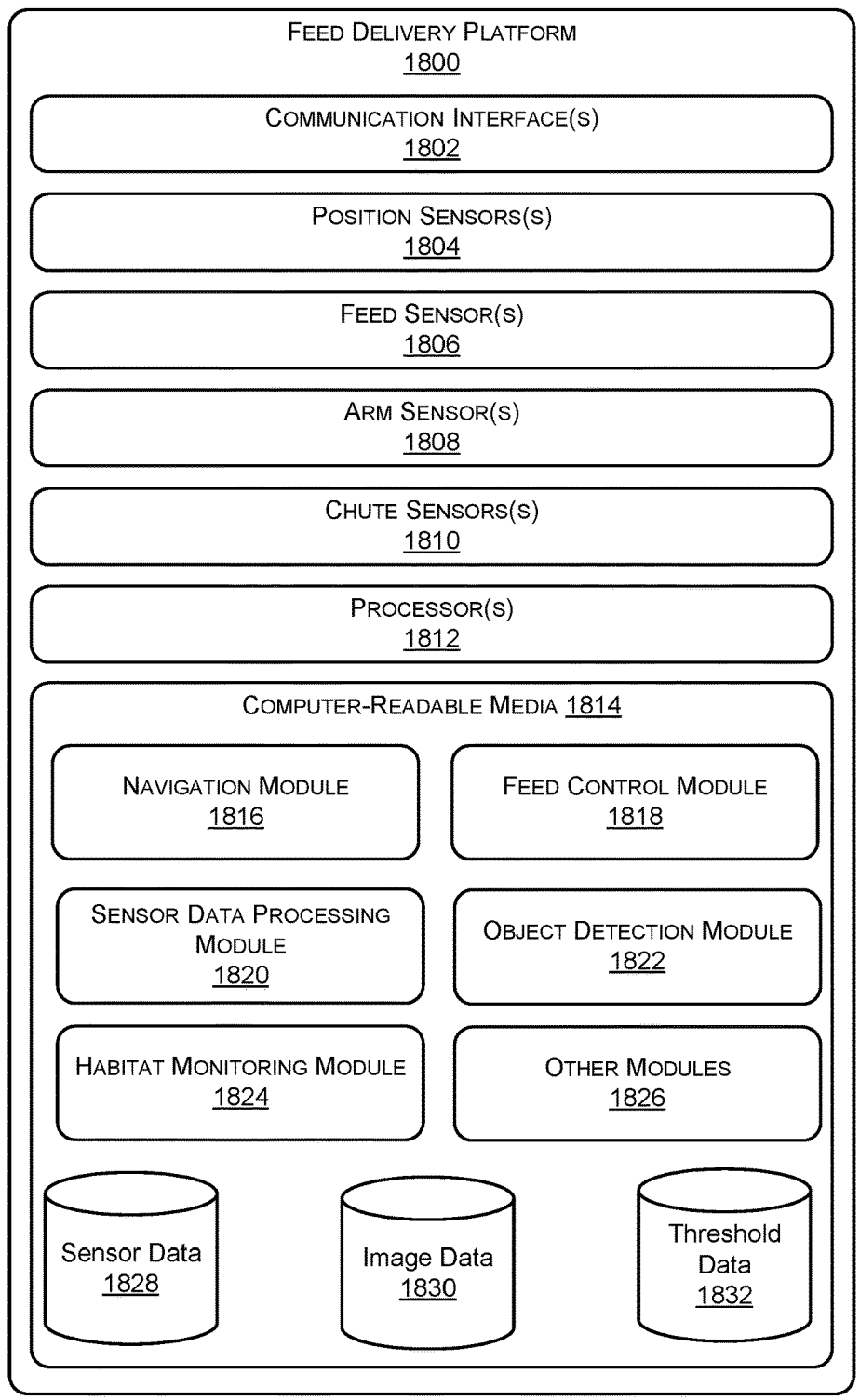
FIG. 18 illustrates example components of a feed delivery platform according to some implementations.

FIG. 18 illustrates example components of a feed delivery platform 1800 according to some implementations. For example, the feed delivery platform 1800 may include a base equipped with a hopper and a feed delivery apparatus support tower. The feed delivery apparatus support tower may include multiple levels each including one or more feed delivery apparatuses for delivering the feed into the habitats. A feed distribution tube may be configured to transfer feed from the hopper to each of the feed delivery apparatuses.

In the illustrated example, the feed delivery platform 1800 includes one or more communication interfaces 1802. The communication interfaces 1802 are configured to facilitate communication between one or more networks and/or other devices, such as other feed delivery platforms, habitats, and/or devices associated with a management system. For instance, the communication interfaces 1802 may provide image and/or sensor data collected during feed deliveries to the management system. In some cases, the communication interfaces 1802 may also facilitate communication between one or more wireless access points, a master device, and/or one or more other computing devices as part of an ad-hoc or local network systems. The communication interfaces 1802 may support both wired and wireless connection to various networks, such as cellular networks, radio, WiFi networks, short-range or near-field networks (e.g., Bluetooth®), infrared signals, local area networks, wide area networks, the Internet, and so forth. In some cases, the communication interfaces 1802 may also enable device to device communication such as between feed delivery platforms and/or one or more other electronic devices in proximity to the feed delivery platform 1800.

The feed delivery platform 1800 may also include various sensors such as position sensors 1804 utilized to assist in navigation through a facility, feed sensors 1806 to monitor a feed level within the hopper, arm sensors 1808 for monitoring conditions of habitats receiving feed, chute sensors 1810 for monitoring an amount of feed being delivered to individual habitat. In some cases, the various sensors 1804-1810 may include light, optical, or photo sensors, mechanical sensors (e.g., pressure, force, or motion sensors), electrical sensors (magnetic, capacitive, resistive, current, or potential based sensors), weight sensors, thermal or heat sensors, among others. In other cases, the sensors 1804-1810 may also be image capturing components, such as cameras and/or video recorders.

The feed delivery platform 1800 may also include one or more processors 1812, such as at least one or more access components, control logic circuits, central processing units, or processors, as well as one or more computer-readable media 1814 to perform the functions associated with the feed delivery platform 1800. Additionally, each of the processors 1812 may itself comprise one or more processors or processing cores.

Depending on the configuration, the computer-readable media 1814 may be an example of tangible non-transitory computer storage media and may include volatile and non-volatile memory and/or removable and non-removable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 1812.

Several modules such as instructions, data stores, and so forth may be stored within the computer-readable media 1814 and configured to execute on the processors 1812. For example, as illustrated, the computer-readable media 1814 stores a navigation module 1816, a feed control module 1818, a sensor data processing module 1820, an object detection module 1822, a habitat monitoring module 1824, as well as other modules 1826. The computer-readable media 1814 may also be configured to store data, such as sensor data 1828 and image data 1830 collected by the sensors 1804-1810 and threshold data 1832.

The navigation module 1816 may be configured to cause the feed delivery platform 1800 to follow a navigation path or to traverse the facility floor to each designated habitat or rack of habitats. For example, the navigation module 1816 may utilize sensor data 1828 and image data 1830 to navigate through the facility. The feed control module 1818 may utilize the sensor data 1828 and the image data 1830 to position the feed delivery apparatus with respect to the habitat and to dispense a desired amount of feed onto each apparatus. For example, the feed control module 1818 may cause a different amount of feed to be distributed to each feed delivery apparatus of the feed delivery platform 1800. The sensor data processing module 1820 may process the sensor data 1828 and the image data 1830 to assist with navigation, feed delivery, object detection, and habitat monitoring. The object detection module 1822 may process the sensor data 1828 and the image data 1830 to determine if an object is blocking the path of the feed delivery platform 1800 as the feed delivery platform 1800 moves throughout the facility. The habitat monitoring module 1824 may process the sensor data 1828 and the image data 1830 to determine an amount of feed to dispense to individual habitats, the health of insects within individual habitats, population count within the habitats, etc.

Figure 19:
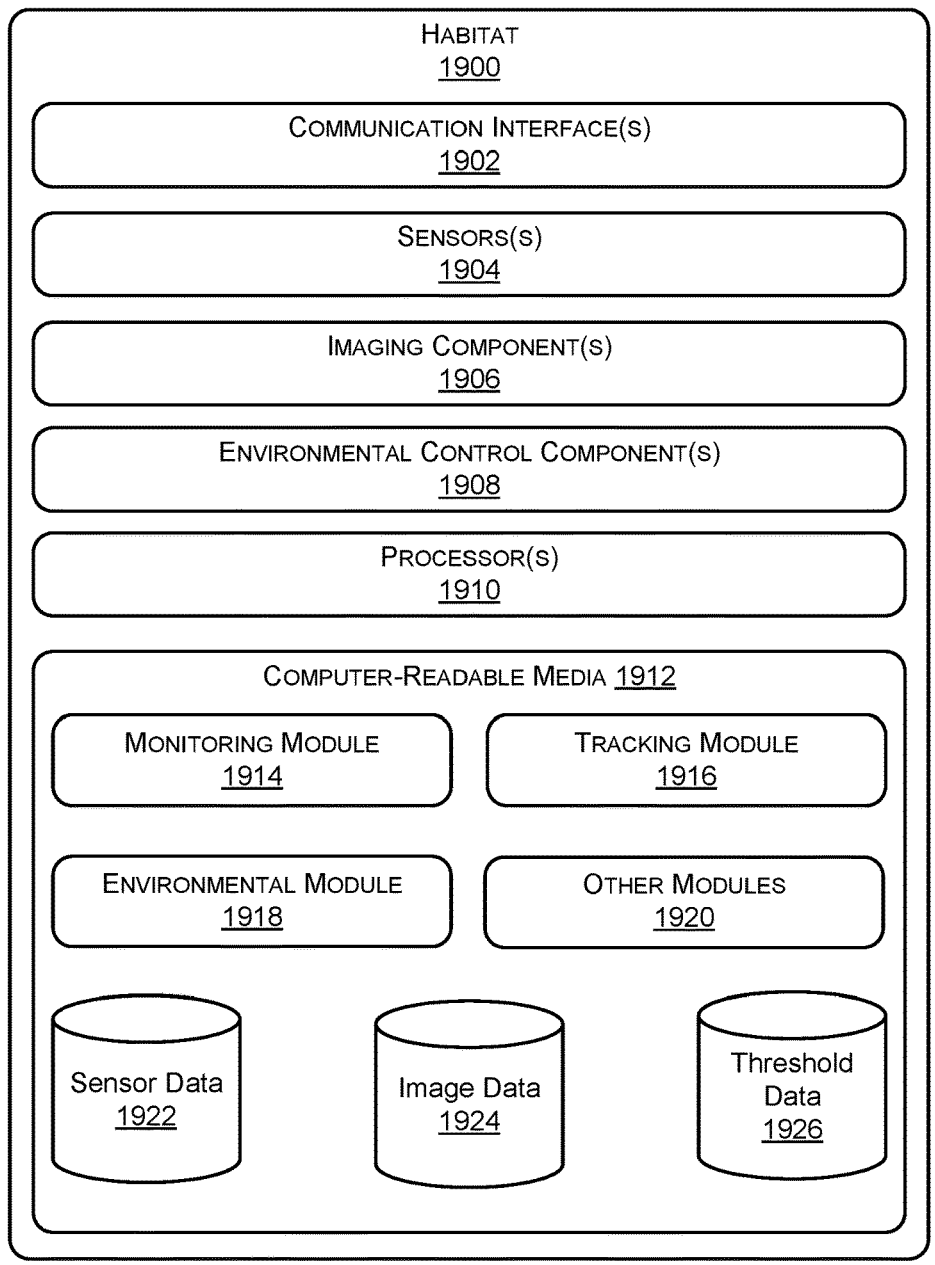
FIG. 19 illustrates example components of a habitat configured to receive feed from a feed delivery platform according to some implementations.

FIG. 19 illustrates example components of a habitat 1900 configured to receive feed from a feed delivery platform according to some implementations. In the illustrated example, the habitat 1900 may be a self-contained unit for cultivating insects. In some cases, the habitat 1900 may be configured to monitor the insects within the habitat 1900 to determine, for example, when the insects should be harvested.

In the illustrated example, the habitat 1900 includes one or more communication interfaces 1902. The communication interfaces 1902 are configured to facilitate communication between one or more networks and/or other devices of the feed delivery system. For instance, the communication interfaces 1902 may provide a notification to the feed delivery platforms or the management system when food levels within the habitat are below a threshold amount. In some cases, the communication interfaces 1902 may also facilitate communication between one or more wireless access points, a master device, and/or one or more other computing devices as part of an ad-hoc or local network system. The communication interfaces 1902 may support both wired and wireless connection to various networks, such as cellular networks, radio, WiFi networks, short-range or near-field networks (e.g., Bluetooth®), infrared signals, local area networks, wide area networks, the Internet, and so forth. In some cases, the communication interfaces 1902 may also enable device to device communication such as between habitats 1900.

The habitat 1900 may also include various sensors 1904 that may collect data that is usable to determine a population, health, insect size, food levels, water levels, etc. within the habitat 1900. For example, the habitat 1900 may include optical, or photo sensors, mechanical sensors (e.g., pressure, force, or motion sensors), electrical sensors (capacitive, resistive, current, or potential based sensors), weight sensors, thermal or heat sensors, among others.

In some cases, a plurality of imaging components 1906 may be used to monitor the insects within the habitat 1900. For example, the habitat 1900 may include a three-dimensional camera system, an infrared camera, and/or a red-green-blue camera. In one example, the three-dimensional and infrared camera may be configured to capture information related to depths, location, and movement of objects within the field of view. The red-green-blue camera may be configured to detect edges of objects by identifying changes in color within the field of view. In some cases, the habitat 1900 may also include additional imaging components for tracking the movement of insects within the habitat 1900. For example, the habitat 1900 may include one or more motion sensors or thermal sensors.

The habitat 1900 may also include one or more environmental control components 1908. The environmental control components 1908 may be utilized to control environmental factors, such as wind, temperatures, humidity, salinity, etc. within the habitat 1900 to encourage proper growth based on life stages and desired crop output.

The habitat 1900 includes one or more processors 1910, such as at least one or more access components, control logic circuits, central processing units, or processors, as well as one or more computer-readable media 1912 to perform the functions associated with the habitat 1900. Additionally, each of the processors 1910 may itself comprise one or more processors or processing cores.

Depending on the configuration, the computer-readable media 1912 may be an example of tangible non-transitory computer storage media and may include volatile and non-volatile memory and/or removable and nonremovable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 1910.

Several modules such as instructions, data stores, and so forth may be stored within the computer-readable media 1912 and configured to execute on the processors 1910. For example, as illustrated, the computer-readable media 1912 stores a monitoring module 1914, a tracking module 1916, an environmental module 1918, as well as other modules 1920. The computer-readable media 1912 may also be configured to store data, such as sensor data 1922 collected by the sensors 1904, image data 1924 captured by the imaging components 1906, and threshold data 1926 such as various desired egg densities or range of densities.

The monitoring module 1914 may be configured to analyze the sensor data 1922 and the image data 1924 and to determine insect size, health, age, movement, activity level, etc. For example, the monitoring module 1914 may be configured to determine when the insects have reached an appropriate size for harvesting and to cause the communication interfaces 1902 to alert another system such as a robotic arm that the threshold has been met to further cause the robotic arm to collect and move the insects to a waste removal and/or processing area.

The tracking module 1916 may be configured to track the movement of insects within the habitat 1900 based on the sensor data 1922 and the image data 1924, and to again cause the communication interfaces 1902 to alert another system such as a robotic arm when the tracking module 1916 determines that a threshold insect size has been reached.

The environmental module 1918 may be configured to analyze the data provided by the monitoring module 1914 and the tracking module 1916 and to determine an environmental adjustment based on the data. For example, the environmental module 1918 may adjust the environmental control components 1908 to a more suitable environment for raising the insects or to encourage certain behavior such as herding, increased feeding, copulation or shedding of the chitin or exoskeleton.

Figure 20:
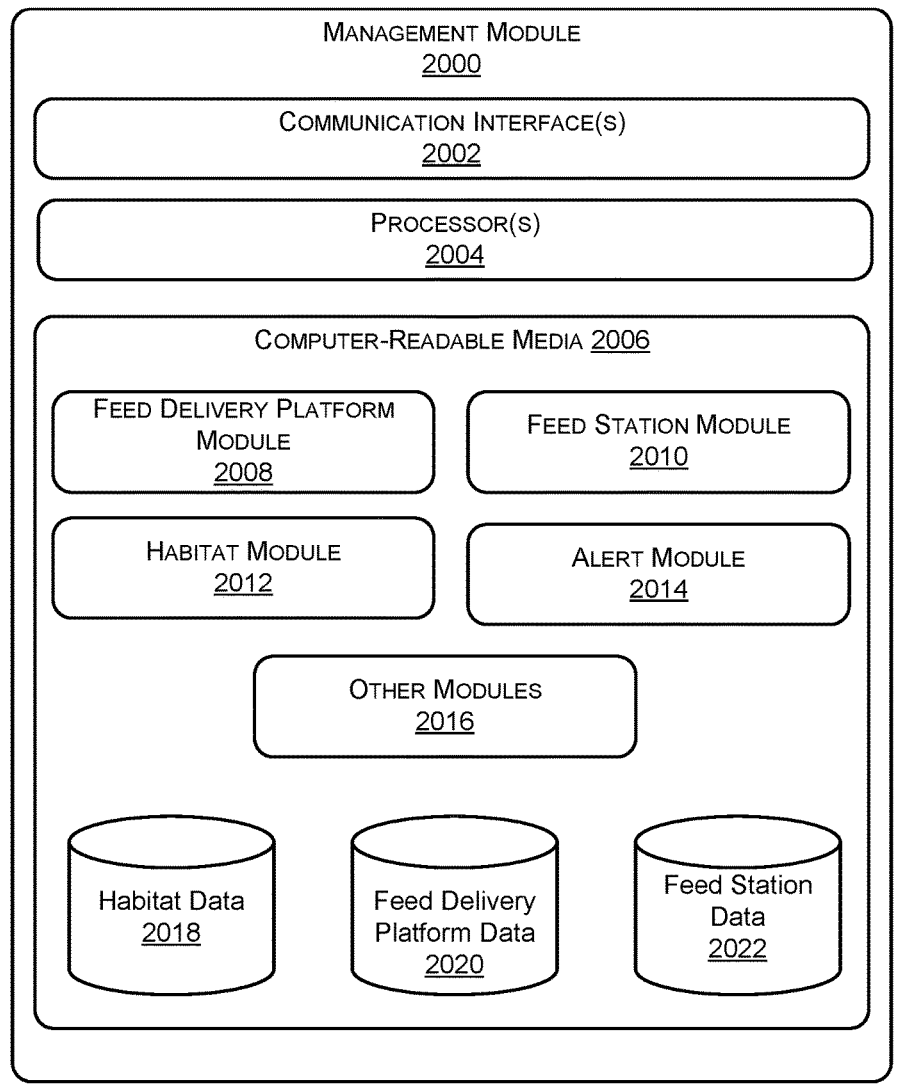
FIG. 20 illustrates example components of a management system associated with one or more feed delivery platforms according to some implementations.

FIG. 20 illustrates example components of a management system 2000 associated with one or more feed delivery platforms according to some implementations. For example, the management system 2000 may be configured to process image and/or sensor data collected within a facility from the feed delivery platforms, habitats, feed station, etc. The management system 2000 may then control and/or coordinate the operation of the feed delivery platforms.

In the illustrated example, the management system 2000 includes one or more communication interfaces 2002. The communication interfaces 2002 are configured to facilitate communication between one or more networks and/or other devices, such as feed delivery platforms, habitats, and/or devices associated with the facility. For instance, the communication interfaces 2002 may provide image and/or sensor data collected during feed deliveries to the management system. In some cases, the communication interfaces 2002 may also facilitate communication between one or more wireless access points, a master device, and/or one or more other computing devices as part of an ad-hoc or local network systems. The communication interfaces 2002 may support both wired and wireless connection to various networks, such as cellular networks, radio, WiFi networks, short-range or near-field networks (e.g., Bluetooth®), infrared signals, local area networks, wide area networks, the Internet, and so forth.

The management system 2000 may also include one or more processors 2004, such as at least one or more access components, control logic circuits, central processing units, or processors, as well as one or more computer-readable media 2006 to perform the functions associated with the management system 2000. Additionally, each of the processors 2004 may itself comprise one or more processors or processing cores.

Depending on the configuration, the computer-readable media 2006 may be an example of tangible non-transitory computer storage media and may include volatile and non-volatile memory and/or removable and nonremovable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 2004.

Several modules such as instructions, data stores, and so forth may be stored within the computer-readable media 2006 and configured to execute on the processors 2004. For example, as illustrated, the computer-readable media 2006 stores a feed delivery platform module 2008, a feed station module 2010, a habitat module 2012, an alert module 2014, as well as other modules 2016. The computer-readable media 2006 may also be configured to store data, such as habitat data 2018 collected and received from the habitats within the facility, feed delivery platform data 2020 collected and received from the feed delivery platforms within the facility, and feed station data 2022 collected and received from the feed stations within the facility.

The feed delivery platform module 2008 may be configured to dispatch and monitor feed delivery platforms based on the habitat data 2018 and the feed delivery platform data 2020. In some cases, the feed delivery platform module 2008 may be configured to provide navigation paths to the feed delivery platforms, lists of habitats that are low on feed, and/or initiation signals to start feed delivery by one or more feed delivery platforms. The feed station module 2010 may be configured to monitor a feed level associated with the feed station using the feed station data 2022. In some cases, the feed station module 2010 may be configured to monitor an amount of feed dispensed to each feed delivery platform associated with the facility.

The habitat module 2012 may be configured to monitor the habitats within the facility using the habitat data 2018 and to cause a feed delivery platform to be dispatched to provide feed when the habitat module 2012 determines the feed level within a habitat has dropped below a threshold. The alert module 2014 may be configured to alert a facility operator to any issues detected within the habitat data 2018, the feed delivery platform data 2020, or the feed station data 2022. For example, if feed delivery platform data 2020 indicated that an object is within the aisle of the facility an alert may be provided to the facility operator.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:
1. A feed delivery platform comprising:
   a communication interface for receiving signals from a control system;
   a base having at least one conveying device for propelling the feed delivery platform through an environment;

a hopper extending upward from and physically coupled to the base, the hopper to hold insect feed;

a support tower extending upward from and physically coupled to the base and adjacent to the hopper;

a first extendable feed delivery apparatus connected to the support tower and positioned above the hopper;

a first sensor mounted to a bottom surface of the base, the first sensor to collect first data, the first data associated with a floor of environment surrounding the feed delivery platform;

a second sensor mounted to a front surface of the base, the second sensor to collect second data, the second data associated with an aisle way of the environment surrounding the feed delivery platform;

a second extendable feed delivery apparatus connected to the support tower, the second extendable feed delivery apparatus positioned above the hopper and horizontally adjacent to the first extendable feed delivery apparatus;

an image capture device;

a feed distribution tube configured to deliver the insect feed from the hopper to the first extendable feed delivery apparatus and the second extendable feed delivery apparatus via a first feed chute connected to the feed distribution tube, wherein the first feed chute includes a first path that distributes the insect feed to the first extendable feed delivery apparatus and a second path that distributes the insect feed to the second extendable feed delivery apparatus;

one or more processors; and computer-readable storage media storing computer-executable instructions, which when executed by the one or more processors cause the one or more processors to:

initiate a feed delivery to one or more habitats in response to receiving a signal at the communication interface, individual ones of the one or more habitats associated with insect populations and wherein the signal includes a navigation path and a list of habitats that are low on feed;

identify a first habitat of the one or more habitats within an environment, based at least in part on the second data;

identify at least one of a marker or identifier within the environment, based at least in part on the first data;

cause the image capture device to collect habitat data associated with at least one habitat of the one or more habitats;

cause the communication interface to wirelessly communicate the habitat data to the control system;

cause the first feed delivery apparatus to orientate with the at least one habitat; and cause the first feed delivery apparatus to deliver a first desired amount of feed into the first habitat.

2. The feed delivery platform as recited in claim 1, wherein the first feed delivery apparatus is positioned opposite the second feed delivery apparatus with respect to the support tower.

3. The feed delivery platform as recited in claim 1, wherein the first feed delivery apparatus is at least one of:
a feed tube;
a conveyor;
a platform.

4. The feed delivery platform system as recited in claim 1, wherein the first extendable feed delivery apparatus, the second extendable feed delivery apparatus are configured to respectively supply the insect feed to first habitat and to a second habitat substantially simultaneously.

5. The feed delivery platform as recited in claim 1, further comprising:
a third extendable feed delivery apparatus connected to the support tower and positioned above the first extendable feed delivery apparatus; and
a fourth extendable feed delivery apparatus connected to the support tower and positioned above the second extendable feed delivery apparatus and horizontally adjacent to the third extendable feed delivery apparatus.

6. A feed delivery platform comprising:
a base having a top surface, a bottom surface, and a side surface, the top surface opposite the bottom surface;
a tower extending upward from the top surface;
at least one conveying device mounted to the side surface of the base;
a sensor mounted to the bottom surface of the base, the sensor to collect data associated with a floor of environment surrounding the feed delivery platform;
a first feed delivery apparatus mounted to the tower;
a second feed delivery apparatus mounted to the tower;
a feed distribution tube mounted to the tower;
a chute connected to the feed distribution tube, the chute having a first path and a second path;
one or more processors; and
computer-readable storage media storing computer-executable instructions, which when executed by the one or more processors cause the one or more processors to:
receive a signal from control system, the signal includes a navigation path and a list of habitats that are low on feed;
determine that the power level associated with the feed delivery platform has met or exceeded a first power threshold;
initiate a feed delivery to one or more habitats in response to determine that the power level is above the first power threshold and receiving the signal from control system;
receive the data from the sensor;
cause the at least one conveying device to orient the feed delivery platform with a first habitat, a second habitat, and at least one of a marker or identifier based at least in part on the navigation path, the list of habitats, and the data;
cause the feed distribution tube to deliver first feed to the first feed delivery apparatus via the first path of the chute and deliver second feed to the second feed delivery apparatus via the second path of the chute;
cause the first feed delivery apparatus to dispense the first feed into the first habitat;
cause the second feed delivery apparatus to dispense the second feed into the second habitat;
determine that a power level associated with the feed delivery platform is below a first power threshold, the first power threshold different than the second power threshold;
identify an available recharge station in response to determining that the power level is below the first power threshold; and
cause the delivery platform to engage with the recharge station to initiate a recharge operation in response to identifying the available recharge station.

7. The feed delivery platform as recited in claim 6, wherein the first feed delivery apparatus dispenses the first feed into the first habitat at substantially the same time as the second feed delivery apparatus dispenses the second feed into the second habitat.

8. The feed delivery platform as recited in claim 6, further comprising:
- a first feed sensor positioned along the first path of the chute, wherein the first feed sensor is configured to collect first feed data associated with the delivery of the first feed to the first feed delivery apparatus; and
- a second feed sensor positioned along the second path of the chute, wherein the second feed sensor is configured to collect second feed data associated with the delivery of the second feed to the second feed delivery apparatus; and
- wherein the computer-readable storage media stores additional computer- executable instructions, which when executed by the one or more processors cause the one or more processors to:
  - determine that a first amount associated with the first feed has met a first feed threshold;
  - cause the chute to close the first path in response to determining the first feed threshold has been met;
  - determine that a second amount associated with the second feed has met a second feed threshold, the second feed threshold different than the first feed threshold; and
  - cause the chute to close the second path in response to determining the second feed threshold has been met.

9. The feed delivery platform as recited in claim 8, further comprising: a hopper accessible to the first path of the chute and the second path of the chute, the hopper configured to hold available feed prior to distribution to the first feed delivery apparatus and the second feed delivery apparatus.

10. The feed delivery platform as recited in claim 6, further comprising:
- a first habitat sensor associated with the feed delivery platform, the first habitat sensor to collect first habitat data associated with the first habitat; and
- a second habitat sensor associated with the feed delivery platform, the second habitat sensor to collect second habitat data associated with the second habitat.

11. The feed delivery platform as recited in claim 10, wherein the computer-readable storage media stores additional computer-executable instructions, which when executed by the one or more processors cause the one or more processors to determine, based at least in part on the first habitat data, a developmental state of an insect population associated with the first habitat.

12. The feed delivery platform as recited in claim 10, further comprising:
- a communication interface to establish a communication channel with a management system; and
- wherein the computer-readable storage media stores additional computer- executable instructions, which when executed by the one or more processors cause the one or more processors to cause the communication interface to send the first habitat data and the second habitat data to the management system.

13. The feed delivery platform as recited in claim 6, wherein the computer-readable storage media stores additional computer-executable instructions, which when executed by the one or more processors cause the one or more processors to cause the at least one conveying device to follow the navigation path through the environment.

14. The feed delivery platform as recited in claim 6, further comprising:
- a communication interface to establish a communication channel with a management system; and
- wherein the computer-readable storage media stores additional computer- executable instructions, which when executed by the one or more processors cause the one or more processors to cause the communication interface to send the data to the management system.

15. A delivery platform comprising:
- a communication interface for receiving signals from a control system;
- a first feed delivery apparatus;
- a second feed delivery apparatus;
- a feed distribution tube configured to deliver feed from a hopper associated with the delivery platform to the first feed delivery apparatus and the second feed delivery apparatus via a chute connected to the feed distribution tube, wherein the chute includes a first feed path that distributes feed to the first feed delivery apparatus and a second feed path that distributes feed to the second feed delivery apparatus;
- an image capture device;
- one or more processors; and
- computer-readable storage media storing computer-executable instructions, which when executed by the one or more processors cause the one or more processors to:
  - initiate a feed delivery to one or more habitats in response to receiving a signal at the communication interface, individual ones of the one or more habitats associated with insect populations and wherein the signal includes a navigation path and a list of habitats that are low on feed;
  - identify a first habitat of the one or more habitats within an environment, based at least in part on the data associated with the environment and the list of habitats;
  - identify at least one of a marker or identifier within the environment, based at least in part on the data associated with the environment;
  - cause the image capture device to collect habitat data associated with the first habitat;
  - cause the communication interface to wirelessly communicate the habitat data to the control system;
  - cause the first feed delivery apparatus to orientate with the first habitat and the at least one of the marker or identifier; and
  - cause the first feed delivery apparatus to deliver a first desired amount of feed into the first habitat.

16. The delivery platform as recited in claim 15, wherein the computer-readable storage media stores additional computer-executable instructions, which when executed by the one or more processors cause the one or more processors to determine the first desired amount of feed prior to delivering the first desired amount of feed into the first habitat.

17. The delivery platform as recited in claim 15, wherein the computer-readable storage media stores additional computer-executable instructions, which when executed by the one or more processors cause the one or more processors to:
- identify a second habitat of the one or more habitats within an environment based at least in part on the data associated with the environment and the list of habitats;
- cause the first feed delivery apparatus to orientate with the second habitat; and
- cause the by the first feed delivery apparatus to deliver a second desired amount of feed into the second habitat, the second desired amount different than the first desired amount.

18. The delivery platform as recited in claim 15, wherein the computer-readable storage media stores additional computer-executable instructions, which when executed by the one or more processors cause the one or more processors to:
- determine that a power level associated with the feed delivery platform is below a first power threshold;

identify an available recharge station in response to determining that the power level is below the first power threshold;

cause the delivery platform to engage with the recharge station to initiate a recharge operation in response to identifying the available recharge station; and determine that the power level associated with the feed delivery platform has met or exceeded a second power threshold, the first power threshold different than the second power threshold.

19. The delivery platform as recited in claim 15, wherein the computer-readable storage media stores additional computer-executable instructions, which when executed by the one or more processors cause the one or more processors to:

determine that an amount of feed stored in the hopper associated with the feed delivery platform is below a first feed threshold;

identify a feed station;

cause the feed delivery platform to orientate the hopper with respect to the feed station to initiate a refill operation;

determine the delivery platform is properly positioned with respect to the feed station;

send a signal to the feed station that the delivery platform is properly position; and determine the amount of feed stored in the hopper has met or exceeded a second feed threshold.

20. The delivery platform as recited in claim 15, wherein the computer-readable storage media stores additional computer-executable instructions, which when executed by the one or more processors cause the one or more processors to:

identify a second habitat of the one or more habitats within an environment at substantially the same time as the feed delivery platform identifies the first habitat;

cause the feed delivery platform to orient the second feed delivery apparatus with the second habitat at substantially the same time as the first feed delivery apparatus orients with the first habitat; and cause the second feed delivery apparatus to deliver a second desired amount of feed into the second habitat at substantially the same time as the first feed delivery platform delivers the first desired amount of feed to the first habitat.

* * * * *